US009789235B2

(12) United States Patent
Gifford et al.

(10) Patent No.: US 9,789,235 B2
(45) Date of Patent: Oct. 17, 2017

(54) SEPARATION AND CONCENTRATION OF PARTICLES

(71) Applicants: Halcyon Biomedical, Incorporated, Friendswood, TX (US); The Administrators of the Tulane Educational Fund, New Orleans, LA (US)

(72) Inventors: Sean C. Gifford, Ft. Edward, NY (US); Sergey S. Shevkoplyas, Friendswood, TX (US)

(73) Assignees: THE ADMINISTRATORS OF THE TULANE EDUCATIONAL FUND, New Orleans, LA (US); HALCYON BIOMEDICAL, INCORPORATED, Friendswood, TX (US)

( * ) Notice: Subject to any disclaimer, the term of this patent is extended or adjusted under 35 U.S.C. 154(b) by 148 days.

(21) Appl. No.: 14/601,205

(22) Filed: Jan. 20, 2015

(65) Prior Publication Data
US 2015/0202549 A1 Jul. 23, 2015

Related U.S. Application Data

(60) Provisional application No. 61/929,357, filed on Jan. 20, 2014.

(51) Int. Cl.
*A61M 1/02* (2006.01)
*A61M 1/36* (2006.01)
(Continued)

(52) U.S. Cl.
CPC ........ *A61M 1/0272* (2013.01); *A61M 1/3672* (2013.01); *A61M 1/3693* (2013.01);
(Continued)

(58) Field of Classification Search
None
See application file for complete search history.

(56) References Cited

U.S. PATENT DOCUMENTS 4,797,211 A * 1/1989 Ehrfeld .................. B01D 61/18
210/321.84
5,427,663 A 6/1995 Austin et al.
(Continued)

FOREIGN PATENT DOCUMENTS

EP 0882464 A2 12/1998
JP 2005124813 A 5/2005

OTHER PUBLICATIONS

Hou, et al. "Microfluidic Devices for Blood Fractionation," Micromachines, 2011, vol. 2, pp. 319-343.
(Continued)

*Primary Examiner* — Krishnan S Menon
(74) *Attorney, Agent, or Firm* — Boulware & Valoir

(57) ABSTRACT

Described are devices, methods, and kits for controlled incremental filtration (CIF), as well as methods of designing CIF devices. For example, a method for CIF may modulate a concentration of particles of a desired size in a fluid. The fluid including the particles may be flowed along a flow path through a central channel to contact a plurality of gaps that fluidically couple the central channel to at least one adjacent side channel network. Flow resistance may be decreased along at least a portion of the flow path effective to modulate the concentration of particles. The method may include selecting the plurality of gaps to be larger than the particles. The method may include causing a consistent flow fraction $f_{gap}$ in the central channel to traverse each gap in the plurality of gaps and flow through the at least one side channel network along the flow path.

22 Claims, 25 Drawing Sheets

(51) Int. Cl.

| | | |
|---|---|---|
| B01D 61/18 | (2006.01) | |
| B01D 61/14 | (2006.01) | |
| B01D 21/24 | (2006.01) | |
| B01D 21/28 | (2006.01) | |
| B01D 21/00 | (2006.01) | |

(52) U.S. Cl.
CPC ......... *A61M 1/3695* (2014.02); *B01D 21/006* (2013.01); *B01D 21/2444* (2013.01); *B01D 21/28* (2013.01); *B01D 61/14* (2013.01); *A61M 2202/0415* (2013.01); *A61M 2202/0427* (2013.01); *A61M 2202/0429* (2013.01); *A61M 2202/0439* (2013.01)

(56) References Cited

U.S. PATENT DOCUMENTS

| | | | |
|---|---|---|---|
| 5,456,824 A | 10/1995 | Misumi et al. | |
| 5,632,906 A | 5/1997 | Ishida et al. | |
| 6,090,251 A * | 7/2000 | Sundberg | B01J 19/0093 204/450 |
| 7,735,652 B2 * | 6/2010 | Inglis | B01L 3/502753 209/155 |
| 7,743,928 B2 * | 6/2010 | Crowley | B01D 61/18 210/321.6 |
| 7,744,762 B2 * | 6/2010 | Lazar | H01J 49/04 210/198.2 |
| 7,806,168 B2 * | 10/2010 | Upadhya | F04B 17/00 165/104.33 |
| 8,071,054 B2 * | 12/2011 | Oh | B01L 3/502761 422/502 |
| 8,186,193 B2 * | 5/2012 | Huang | E05B 27/0057 70/367 |
| 8,221,604 B2 * | 7/2012 | Yano | B01D 57/02 204/450 |
| 2004/0248167 A1 * | 12/2004 | Quake | B01F 5/0646 435/6.19 |
| 2006/0118479 A1 | 6/2006 | Shevkoplyas et al. | |
| 2007/0160503 A1 | 7/2007 | Sethu et al. | |
| 2007/0282242 A1 | 12/2007 | Gibbs et al. | |
| 2008/0023399 A1 | 1/2008 | Inglis et al. | |
| 2013/0168298 A1 | 7/2013 | Huang et al. | |
| 2013/0226150 A1 | 8/2013 | Nash et al. | |

OTHER PUBLICATIONS

Gossett, et al. "Label-free Cell Separation and Sorting in Microfluidic Systems," Anal. Bioanal. Chem., 2010, v. 397, pp. 3249-3267.
Sethu, et al. "Microfluidic Diffusive Filter for Apheresis (Leukapheresis)," Lab Chip, 2006, v. 6, pp. 83-89.
Gifford, et al. "Controlled Incremental Filtration: A Simplified Approach to Design and Fabrication of High-Throughput Microfluidic Devices for Selective Enrichment of Particles," Lab Chip, 2014, v. 14, pp. 4496-4505.
Chen, et al. "Microfluidic Chip for Blood Cell Separation and Collection Based Crossflow Filtration," Sens. Actuators, B, 2008, v. 130, pp. 216-221.
Yung, et al. "Micromagnetic-Microfluidic Blood Cleansing Device," Lab Chip, 2009, v. 9, pp. 1171-1177.
Shevkoplyas, et al. "Biomimetic Autoseparation of Leukocytes from Whole Blood in Microfluidic Device," Anal. Chem., 2005, v. 77, pp. 933-937.
Zhang, et al. "Effect of Exposure Dose on the Replication Fidelity and Profile of Very High Aspect Ratio Microchannels in SU-8," Lab Chip, 2004, v. 4, pp. 646-653.
Tanyeri, et al. "A Microfluidic-based Hydrodynamic Trap: Design and Implementation," Lab Chip, 2011, v. 11, pp. 1786-1794.
Kersaudy-Kerhoas, et al. "Micro-scale Blood Plasma Separation: From Acoustophoresis to Egg-beaters," Lab Chip, 2013, v. 13, pp. 3323-3346.
Yamada, et al. "Hydrodynamic Filtration for On-Chip Particle Concentration and Classification Utilizing Microfluidics," Lab Chip, 2005, v. 5, pp. 1233-1239.
Yamada, et al. "Pinched Flow Fractionation: Continuous Size Separation of Particles Utilizing a Laminar Flow Profile in a Pinched Microchannel," Anal. Chem., 2004, v. 76, pp. 5465-5471.
Zhao, et al. "Shear-induced Particle Migration and Margination in a Cellular Suspension," Phys. Fluids, 2012, v. 24, pp. 011902-1-011902-21.
Quek, et al. "Separation of Deformable Particles in Deterministic Lateral Displacement Devices," Phys. Rev. E: Stat., Nonlinear, Soft Matter Phys., 2011, v. 83, pp. 056301-1-056301-7.
Inglis, et al. "A Scalable Approach for High Throughput Branch Flow Filtration," Lab Chip, 2013, v. 13, pp. 1724-1731.
Zhang, et al. "An All-in-One Microfluidic Device for Parallel DNA Extraction and Gene Analysis," Biomed. Microdevices, 2010, v. 12, pp. 1043-1049.
Sollier, et al. "Size-Selective Collection of Circulating Tumor Cells Using Vortex Technology," Lab Chip, 2014, v. 14, pp. 63-77.
Seo, et al. "Membrane-free Microfiltration by Asymmetric Inertial Migration," Appl. Phys. Lett., 2007, v. 91, pp. 033901-1-033901-3.
Hou, et al. "Isolation and Retrieval of Circulating Tumor Cells Using Centrifugal Forces," Sci. Rep. 2013, v. 3, pp. 1259-1267.
Alves, et al. "Isolation of Antibiotics from Industrial Fermentation Broths Using Membrane Technology," Desalination, 2002, v. 148, pp. 181-186.
Yang, et al. "A Microfluidic Device for Continuous, Real Time Blood Plasma Separation," Lab Chip, 2006, v. 6, 871-880.
Di Carlo, "Inertial Microfluidics," Lab Chip, 2009, v. 9, pp. 3038-3046.
Doyeux, et al. "Spheres in the Vicinity of a Bifurcation: Elucidating the Zweifach-Fung Effect," J. Fluid Mech., 2011, v. 674, pp. 359-388.
Inglis, et al. "Critical Particle Size for Fractionation by Deterministic Lateral Displacement," Lab Chip, 2006, v. 6, pp. 655-658.
Singh, et al. Fabrication and Characterization of HAR Microfluidic Device to Concentrate Microalgae. In Nanotechnology 2012: Electronics, Devices, Fabrication, MEMS, Fluidics, and Computational (vol. 2); Chapter 3: MEMS and NEMS Devices and Applications; 2012, pp. 157-160.
Pamme, N., "Continuous Flow Separations in Microfluidic Devices," Lab Chip, 2007, v. 7, No. 12, p. 1644-1659.
International Search Report dated May 20, 2015 for related application PCT/US2015/012107 filed Jan. 20, 2015.
Written Opinion dated May 20, 2015 for related application PCT/US2015/012107 filed Jan. 20, 2015.
International Search Report dated May 29, 2015 for related application PCT/US2015/012108 filed Jan. 20, 2015.
Written Opinion dated May 29, 2015 for related application PCT/US2015/012108 filed Jan. 20, 2015.

* cited by examiner

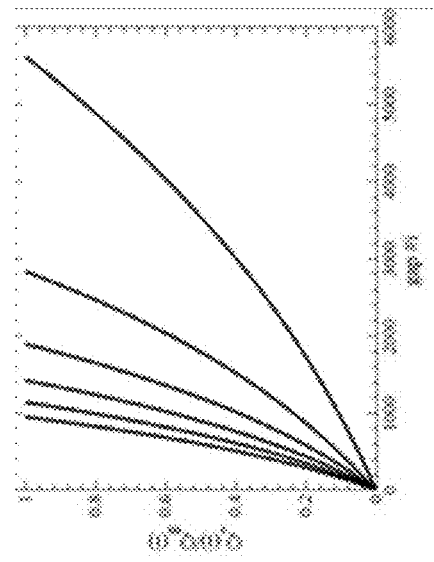
FIG. 10-A
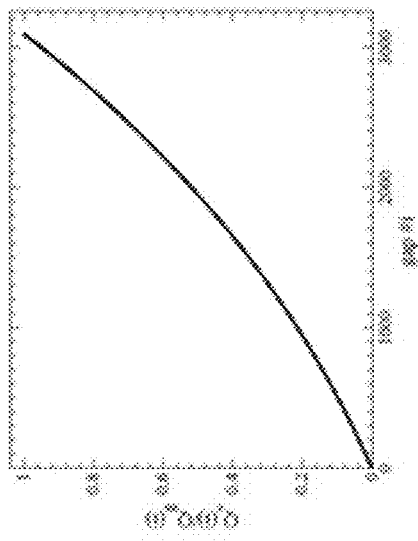
FIG. 10-B
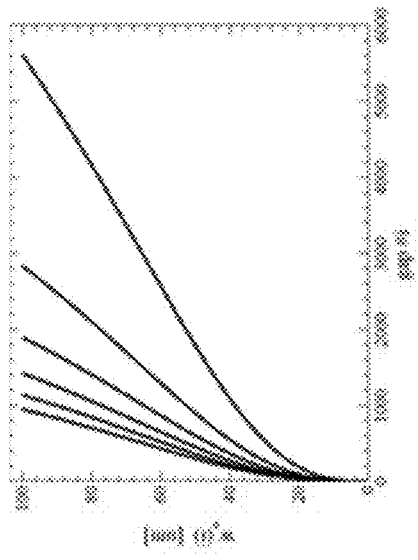
FIG. 10-C
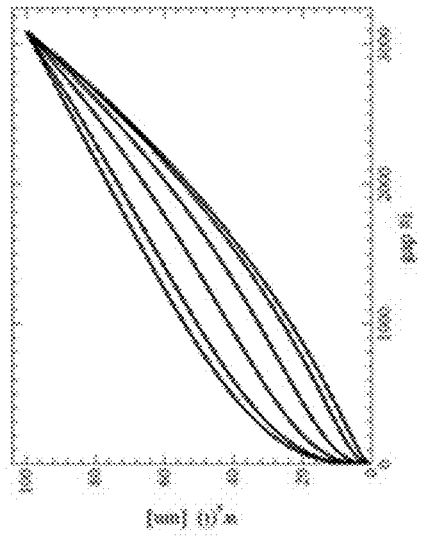
FIG. 10-D

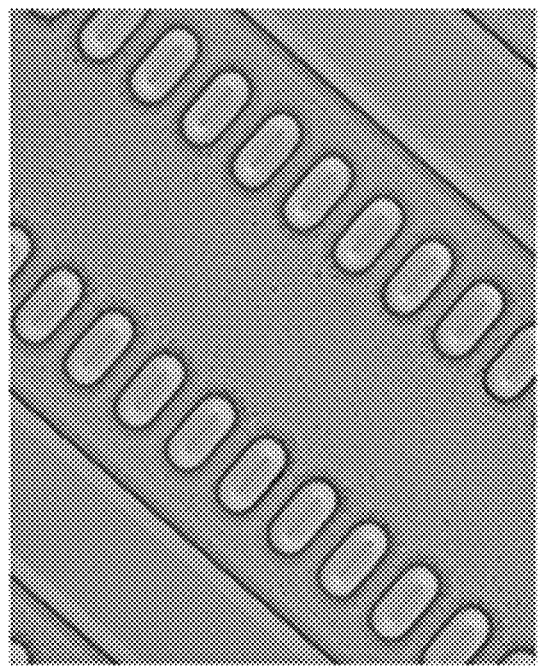
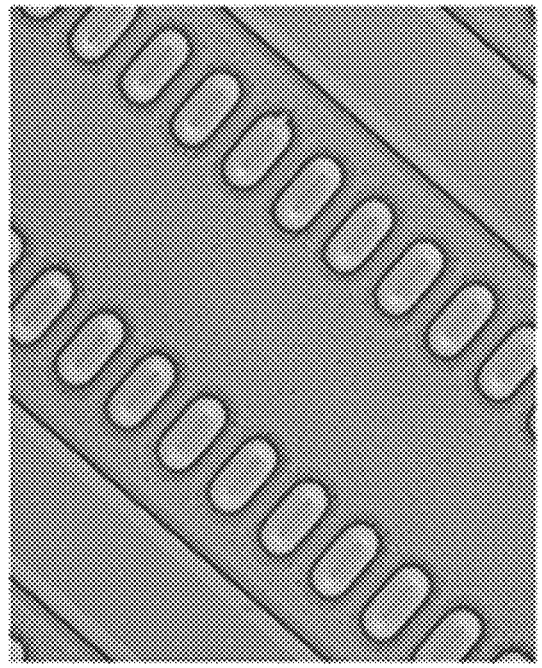
FIG. 12A

SEPARATION AND CONCENTRATION OF PARTICLES

CROSS-REFERENCE TO RELATED APPLICATIONS

This application claims priority to U.S. Provisional Patent Application No. 61/929,357, filed on Jan. 20, 2014, which is incorporated by reference herein in its entirety.

STATEMENT REGARDING FEDERALLY SPONSORED RESEARCH

This invention was made with United States government support under federal STTR contract no. W81XWH-11-C-0008 awarded by the Department of Defense. The United States government may have certain rights in this invention.

BACKGROUND

Manipulation of particles by size in an aqueous suspension or slurry may have widespread applications. Particles may be concentrated or retained for subsequent processing, diagnostic testing, or storage, e.g., algae spore concentration, circulating tumor cell (CTC) enrichment, whole blood processing, and the like. Undesirable particles may be separated from other components, e.g., extraction of antibiotics from fermentation broth, DNA purification, blood plasma cleansing, wastewater treatment, and the like.

Macroscopic methods, such as dead-end filtration and centrifugation may be time-consuming, may be unsuited to continuous processing, may cause the particles to be exposed to undesirable conditions such as large shear forces or prolonged contact with foreign surfaces, may cause filter fouling, and may require bulky, expensive equipment. Tangential flow or cross-flow filtration may not be cost-effective for many applications, particularly for one-time use requirements due to contamination or sterility concerns, e.g., blood cell separation.

Continuous microfluidic techniques may include active devices using magnetic, acoustic, dielectrophoretic, or other forces, but may require complex equipment or undesirable solution preparation steps, and may also be low throughput. Passive techniques may use microfluidic phenomena, such as deterministic lateral displacement (DLD), the Zweifach-Fung effect, pinched flow fraction, hydrodynamic filtration, etc., or inertial focusing such as in the tubular pinch effect and dean flow fractionation. However, microfluidics may be problematic for small particles below ~5 µm, leading to the use of high pressures which may damage sensitive particles, such as platelets or cells. Microfluidic devices may require computational fluid dynamics (CFD) simulations, particularly for manipulating particles of a specific size. Such CFD techniques may be complex, time consuming, and may be limited by particle heterogeneity, especially for biological applications, as well as the constraints of finite computing power.

One area in need of improved particle separation technique is blood cell separation. Over 30 million individual units of the three main blood components—red blood cells (RBCs), platelet concentrate (PC), and plasma—are transfused in the U.S. every year. Nearly 70% of all whole blood (WB) donated in the U.S. is collected on mobile blood drives, often more than 100 miles away from the centralized blood banking facilities. Because of the significant differences in optimal storage conditions (1-6° C. for RBCs, 22±2° C. for platelets, −18° C. for plasma), WB should be quickly separated. The centrifugation-based equipment currently used to process WB into blood components may be undesirably expensive, bulky, laborious, and energy-intensive, especially for mobile blood collection coaches.

Further, high-speed centrifugation for WB separation may subject blood cells to damaging physical forces, may require two stages of centrifugation to separate WB into packed RBCs and platelet-rich plasma (PRP), followed by PRP into PC and platelet-poor plasma (PPP).

The present application appreciates that manipulation of particles by size in an aqueous suspension or slurry may be a challenging endeavor.

SUMMARY

In one embodiment, a controlled incremental filtration (CIF) device is provided. The CIF device may be configured for modulating a concentration of particles of a desired size in a microfluidic flow. The CIF device may include a substrate. The substrate may include at least one CIF module. The substrate may define in each CIF module a central channel. The central channel may extend along a flow path between a central channel flow input and a central channel flow output. The substrate may define a plurality of micro-features adjacent to the central channel. The plurality of micro-features may define a plurality of gaps. The plurality of micro-features may separate the central channel from at least one side channel network. The plurality of gaps may be configured to fluidically couple the central channel to the at least one side channel network. The at least one side channel network may extend along the central channel to at least one side channel output. The at least one side channel network may include one or more of a first side channel network portion and a second side channel network portion.

In the CIF device, the first side channel network portion may include: a plurality of side channel curves adjacent to the central channel, at least a portion of the plurality of micro-features, and at least a portion of the plurality of gaps. The plurality of side channel curves may be characterized by a corresponding plurality of lengths that decrease along the flow path. Each side channel curve may fluidically couple at least one gap of the plurality of gaps in the first side channel network portion to one or more of: an adjacent gap in the plurality of gaps and an adjacent curve in the plurality of curves.

In the CIF device, the second side channel network portion may include: a side channel adjacent to the central channel, at least a portion of the plurality of micro-features, and at least a portion of the plurality of gaps. The side channel may be characterized by a flow cross-section. The flow cross-section may increase along the flow path such that the plurality of gaps in second side channel network portion are characterized by one or more of: a consistent flow fraction $f_{gap}$ and a plurality of different gap volumetric flow rates.

In the CIF device, the at least one side channel network may be characterized by a decreasing flow resistance along at least a portion of the flow path effective to modulate the concentration of particles of the desired size in the microfluidic flow.

In another embodiment, a method for controlled incremental filtration (CIF) is provided. The method may modulate a concentration of particles of a desired size in a fluid. The method may include providing the fluid comprising the particles of the desired size. The method may include flowing the fluid including the particles of the desired size along a flow path through a central channel. The central channel may include a plurality of gaps that fluidically couple the central channel to at least one adjacent side channel network. The method may include decreasing flow resistance along at least a portion of the flow path effective to modulate the concentration of particles by contacting the fluid including the particles of the desired size to the plurality of gaps. The method may include selecting the plurality of gaps including an average flow cross-section larger than the particles of the desired size. The method may include causing different gap volumetric flow rates among at least a portion of the plurality of gaps. The method may include causing a consistent flow fraction $f_{gap}$ in the central channel to traverse each gap in the plurality of gaps and flow through the at least one side channel network along the flow path.

In one embodiment, a method for designing a controlled incremental filtration (CIF) device is provided. The CIF device may modulate a concentration of particles of a desired size in a fluid. The method may include preparing a design for a CIF device. The design for the CIF device may include a central channel. The central channel may extend along a flow path between a central channel flow input and a central channel flow output. The design for the CIF device may include at least one side channel network adjacent to the central channel. The at least one side channel network may extend along the flow path to at least one side channel output. The central channel may be separated from the at least one side channel by a plurality of micro-features. The plurality of micro-features may define a plurality of gaps i. The plurality of gaps may be configured to fluidically couple the central channel and the at least one side channel through the plurality of micro-features. The method may include selecting a desired flow fraction $f_{gap}$ for the CIF device. The method may include determining a plurality of adjusted dimensions along the flow path. The method may include adapting the CIF device design to incorporate the plurality of the adjusted dimensions effective to provide a decreasing flow resistance along at least a portion of the flow path effective to modulate the concentration of particles of the desired size in the fluid.

In another embodiment, a kit is provided. The kit may include a controlled incremental filtration (CIF) device configured for modulating a concentration of particles of a desired size in a microfluidic flow. The CIF device may include substrate. The substrate may include at least one CIF module. The substrate may define in each CIF module a central channel. The central channel may extend along a flow path between a central channel flow input and a central channel flow output. The substrate may define a plurality of micro-features adjacent to the central channel. The plurality of micro-features may define a plurality of gaps. The plurality of micro-features may separate the central channel from at least one side channel network. The plurality of gaps may be configured to fluidically couple the central channel to the at least one side channel network. The at least one side channel network may extend along the central channel to at least one side channel output. The at least one side channel network may include one or more of a first side channel network portion and a second side channel network portion.

In the CIF device, the first side channel network portion may include: a plurality of side channel curves adjacent to the central channel, at least a portion of the plurality of micro-features, and at least a portion of the plurality of gaps. The plurality of side channel curves may be characterized by a corresponding plurality of lengths that decrease along the flow path. Each side channel curve may fluidically couple at least one gap of the plurality of gaps in the first side channel network portion to one or more of: an adjacent gap in the plurality of gaps and an adjacent curve in the plurality of curves.

In the CIF device, the second side channel network portion may include: a side channel adjacent to the central channel, at least a portion of the plurality of micro-features, and at least a portion of the plurality of gaps. The side channel may be characterized by a flow cross-section. The flow cross-section may increase along the flow path such that the plurality of gaps in second side channel network portion are characterized by one or more of: a consistent flow fraction $f_{gap}$ and a plurality of different gap volumetric flow rates.

In the CIF device, the at least one side channel network may be characterized by a decreasing flow resistance along at least a portion of the flow path effective to modulate the concentration of particles of the desired size in the microfluidic flow.

The kit may include a set of instructions. The set of instructions may include directions to a user to provide the fluid comprising the particles of the desired size. The set of instructions may include directions to a user to flow the fluid including the particles of the desired size along a flow path through the central channel. The set of instructions may include directions to a user to decrease flow resistance along at least a portion of the flow path effective to modulate the concentration of particles by contacting the fluid comprising the particles of the desired size to the plurality of gaps. The set of instructions may include directions to a user to select the plurality of gaps including an average flow cross-section larger with respect to the particles of the desired size. The set of instructions may include directions to a user to cause different gap volumetric flow rates among at least a portion of the plurality of gaps. The set of instructions may include directions to a user to cause a consistent flow fraction $f_{gap}$ in the central channel to traverse each gap in the plurality of gaps and flow through the at least one side channel network along the flow path.

BRIEF DESCRIPTION OF THE DRAWINGS

The accompanying figures, which are incorporated in and constitute a part of the specification, illustrate example methods and apparatuses, and are used merely to illustrate example embodiments.

FIG. 1-A is a block diagram illustrating an exemplary CIF device.

FIG. 1-B is a diagram illustrating a first side channel network portion of an exemplary CIF device.

FIG. 1-C is a diagram illustrating a first side channel network portion of an exemplary CIF device.

FIG. 1-D is a side cross-section view along a flow path of an exemplary CIF device.

FIG. 1-E is a close-up top view along a flow path of an exemplary CIF device.

FIG. 1-F is a close-up perspective view of an exemplary CIF device.

FIG. 1-G is a top view along a flow path of an exemplary CIF device.

FIG. 1-H is a cross section view perpendicular to a flow path of an exemplary CIF device.

FIG. 2-B is a block diagram of a CIF device including two CIF modules fluidically coupled in parallel.

FIGS. 10-A, 10-B, 10-C, and 10-D are a series of graphs illustrating the dependence of device length and side channel width on input parameters such as desired device depth d and degree of flow fraction $f_{gap}$.

FIG. 10-A is a graph demonstrating an inverse correlation between the total number of gaps for achieving a given total degree of particle filtration/enrichment and the value of $f_{gap}$, which decreases linearly from $5.76 \times 10^{-3}$ to $9.6 \times 10^{-5}$ in the curves from left-to-right.

FIG. 10-B is a graph demonstrating that side channel width $w_s(i)$ may increase at each subsequent gap while the ratio of side channel flow to central channel flow may increase toward a unit endpoint condition, for the same values of $f_{gap}$ as in FIG. 10-A.

FIG. 10-C is a graph demonstrating a depth-dependence of the $w_s(i)$ curve for a variety of depths (left-to-right: 150 μm, 100 μm, 50 μm, 25 μm, 10 μm, 5 μm), while $f_{gap}$ is held constant at $1.76 \times 10^{-4}$.

FIG. 10-D is a graph demonstrating that when $f_{gap}$ is constant, the six cases in FIG. 10-C generate the same relative flow fraction curve, independent of device depth.

FIG. 12-A is a micrograph showing the transition between platelet retention in the central channel (left panel) and platelet loss (right panel) in a parallel array of test device segments with a range of flow fraction $f_{gap}$ values, and a given value of $w_c$.

FIG. 12-B is schematic showing that long-length devices with the given parameters are easily patterned for photomask creation.

FIG. 12-C is a micrograph image of the output of a representative device during operation showing that greater than 85% of platelets may be retained in the central channel, representing about three times enrichment in particle concentration.

FIG. 13-A is a schematic illustrating a CIF device with end side channel widths much larger than that of the central channel.

FIG. 13-B is an image of the input of the CIF device showing the 1.5-4 μm platelets and 8.3 μm particles in the central channel.

FIG. 13-C is an image of the output of the CIF device showing selective retention and concentration of the large 8.3 μm diameter particles compared to the platelets.

DETAILED DESCRIPTION

Figure 1A:
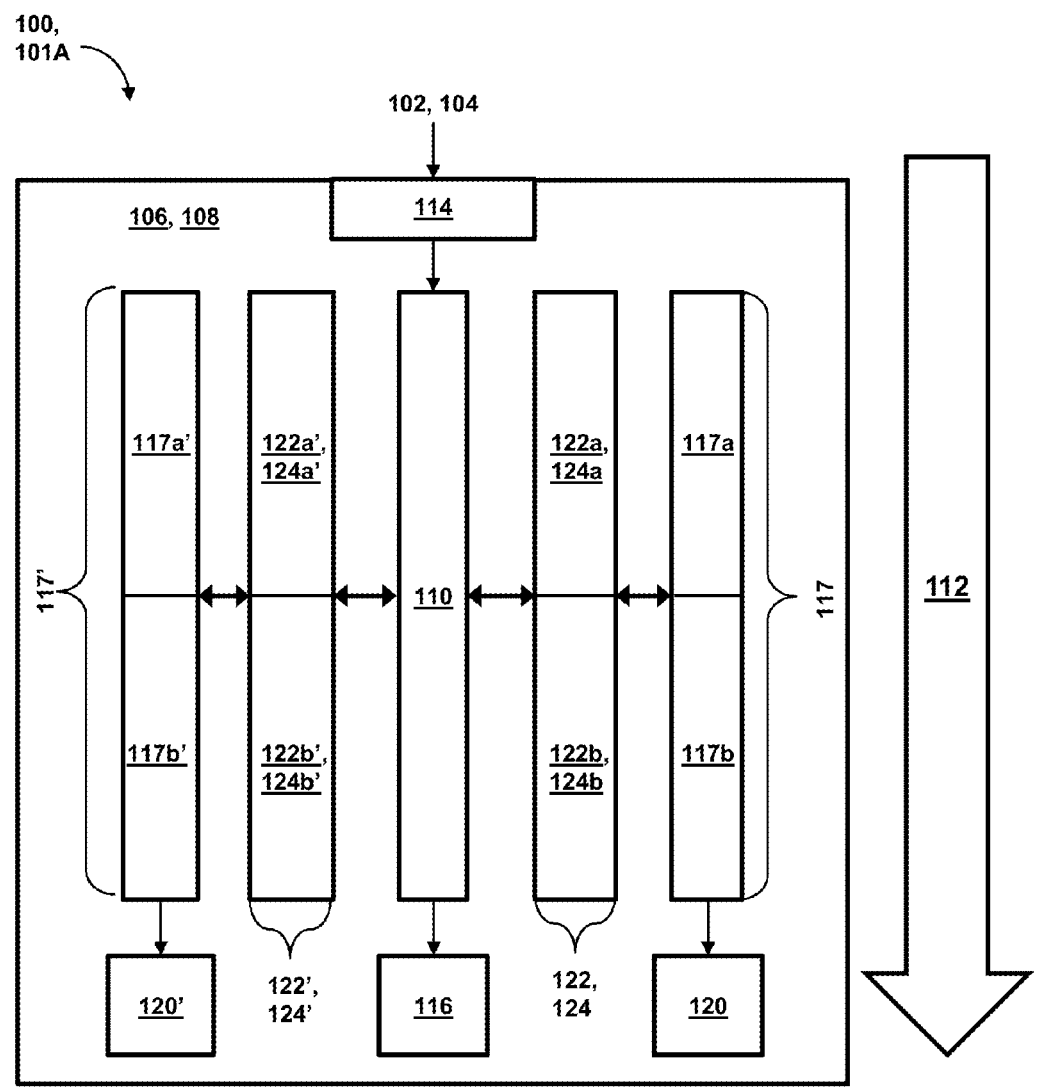
FIGS. 1-A, 1-B, 1-C, 1-D, 1-E, 1-F, 1-G, and 1-H depict various views of an exemplary CIF device.
Figure 1B:
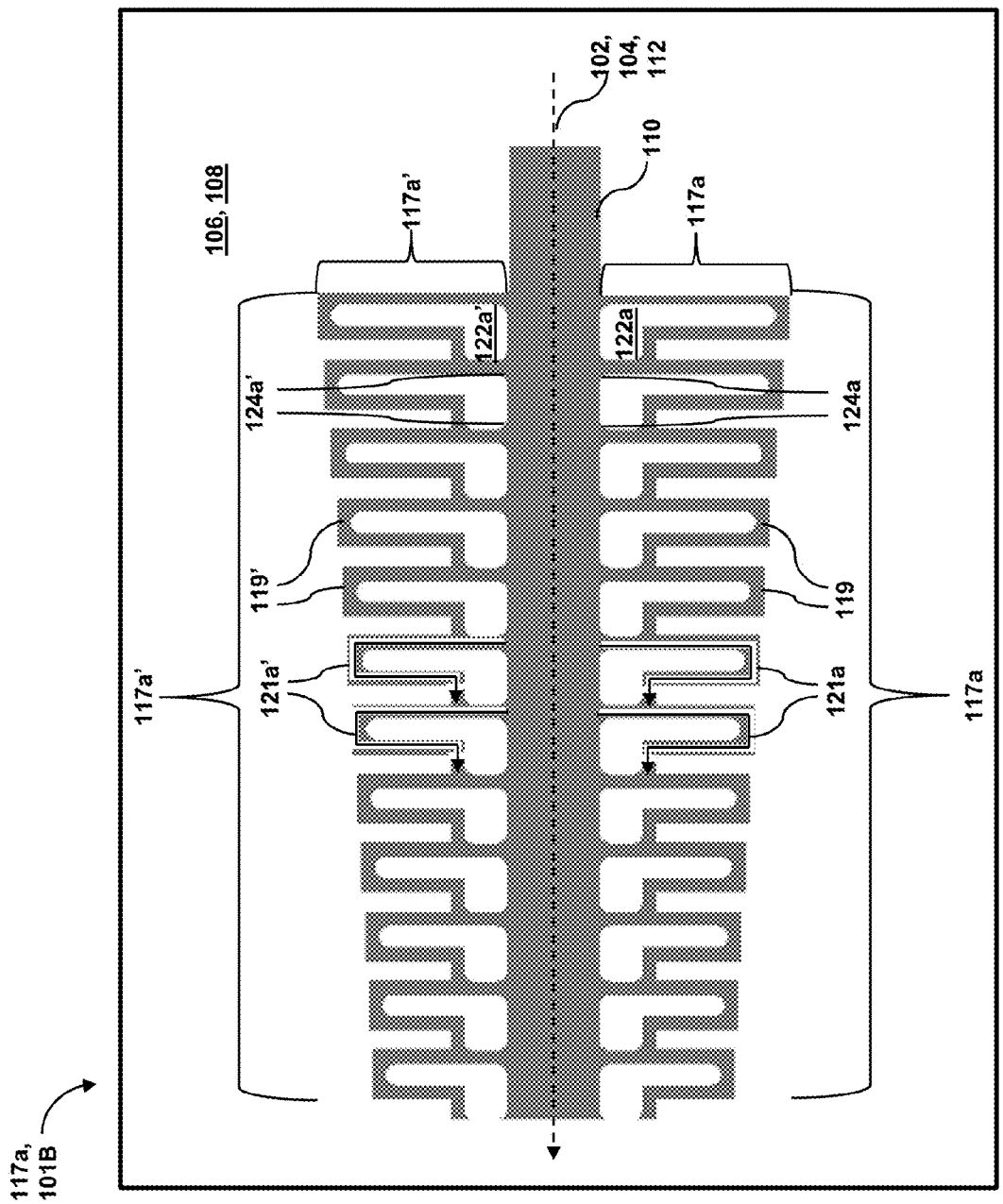

FIGS. 1-A, 1-B, 1-C, 1-D, 1-E, 1-F, 1-G, and 1-H depict various views of an exemplary CIF device 100 or portions thereof. FIG. 1-A is a block diagram 101A illustrating various aspects of an exemplary CIF device 100. CIF device 100 may be configured for modulating a concentration of particles 102 of a desired size in a microfluidic flow 104. It is to be understood that microfluidic flow 104 may include fluids for testing, e.g., to determine whether significant amounts of particles 102 of the desired size are present. CIF device 100 may include a substrate 106. Substrate 106 may include at least one CIF module 108. Substrate 106 may define in each CIF module 108 a central channel 110. Central channel 110 may extend along a flow path 112 between a central channel flow input 114 and a central channel flow output 116. Substrate 106 may define a plurality of micro-features 122 adjacent to central channel 110. Plurality of micro-features 122 may define a plurality of gaps 124. Plurality of micro-features 122 may separate central channel 110 from at least one side channel network 117. Plurality of gaps 124 may be configured to fluidically couple central channel 110 to side channel network 117. Side channel network 117 may extend along central channel 110 to at least one side channel output 120. Side channel network 117 may include one or more of a first side channel network portion 117a and a second side channel network portion 117b. In CIF device 100, side channel network 117 may be characterized by a decreasing flow resistance along at least a portion of flow path 112 effective to modulate concentration of particles 102 of the desired size in microfluidic flow 104. In various embodiments, the plurality of gaps 124a in first side channel network portion 117a are characterized by one or more of: a consistent flow fraction $f_{gap}$ and a plurality of different gap volumetric flow rates. In some embodiments, the plurality of gaps 124 in side channel network 117 are characterized by one or more of: a consistent flow fraction $f_{gap}$ and a plurality of different gap volumetric flow rates.

FIG. 1-B is a top view schematic 101B illustrating various aspects of first side channel network portion 117a, including features illustrated in block form in FIG. 1-A, such as microfluidic flow 104, substrate 106, CIF module 108, central channel 110, flow path 112, plurality of micro-features 122a, and plurality of gaps 124a. Further, for example, first side channel network portion 117a may include a plurality of side channel curves 119 adjacent to central channel 110. First side channel network portion 117a may include least a portion of plurality of micro-features 122a, and at least a portion of plurality of gaps 124a. Plurality of side channel curves 119 may be characterized by a corresponding plurality of lengths 121a that decrease along flow path 112. Each side channel curve 119 may fluidically couple at least one gap of plurality of gaps 124a in first side channel network portion 117a to one or more of: an adjacent gap in plurality of gaps 124a and an adjacent curve in plurality of curves 119.

FIG. 1-C is a top view schematic 101C illustrating various aspects of second side channel network portion 117b, including features illustrated in block form in FIG. 1-A, such as particles 102, microfluidic flow 104, substrate 106, CIF module 108, central channel 110, flow path 112, central channel flow input 114, central channel flow output 116, plurality of micro-features 122*a*, plurality of gaps 124*a*, and side channel output 120. Further, for example, second side channel network portion 117*b* may include a side channel 118 adjacent to central channel 110. Second side channel network portion 117*b* may include at least a portion of plurality of micro-features 122*b*. Second side channel network portion 117*b* may include at least a portion of plurality of gaps 124*b*. Side channel 118 may be characterized by a flow cross-section 139 (see FIG. 1-H). Flow cross-section 139 may increase along flow path 112 such that plurality of gaps 124*b* in second side channel network portion 117*b* are characterized by one or more of: a consistent flow fraction $f_{gap}$ and a plurality of different gap volumetric flow rates.

Referring again to FIG. 1-A, in some embodiments, side channel network 117 may include first side channel network portion 117*a* followed by second side channel network portion 117*b* in sequence along flow path 112. In several embodiments, CIF device 100 may include two of side channel networks 117, 117'. Side channel networks 117, 117' may be adjacent to central channel 110. For example, two side channel networks 117, 117' may be separated by central channel 110 and may be located on either side of central channel 110.

Referring to FIG. 1-B, for example, for two side channel networks 117, 117', substrate 106 may define two first side channel networks 117*a*, 117*a'* including at least two pluralities of side channel curves 119, 119' adjacent to central channel 110 and at least two pluralities of micro-features 122*a*, 122*a'*. At least two pluralities of side channel curves 119, 119' may be characterized by at least two corresponding pluralities of lengths 121*a*, 121*a'* that decrease along flow path 112. Central channel 110 may be separated from each of at least two pluralities of side channel curves 119, 119' by each plurality of micro-features 122*a*, 122*a'*. At least two pluralities of micro-features 122*a*, 122*a'* may define at least two pluralities of gaps 124*a*, 124*a'*. At least two pluralities of gaps 124*a*, 124*a'* may be configured to fluidically couple central channel 110 and pluralities of side channel curves 119, 119' through pluralities of micro-features 122*a*, 122*a'*. Each of pluralities of side channel curves 119, 119' may fluidically couple at least one corresponding gap of pluralities of gaps 124*a*, 124*a'* in first side channel network portion 117*a* to one or more of: an adjacent corresponding gap in pluralities of gaps 124*a*, 124*a'* and an adjacent corresponding curve in pluralities of side channel curves 119, 119'.

Figure 1C:
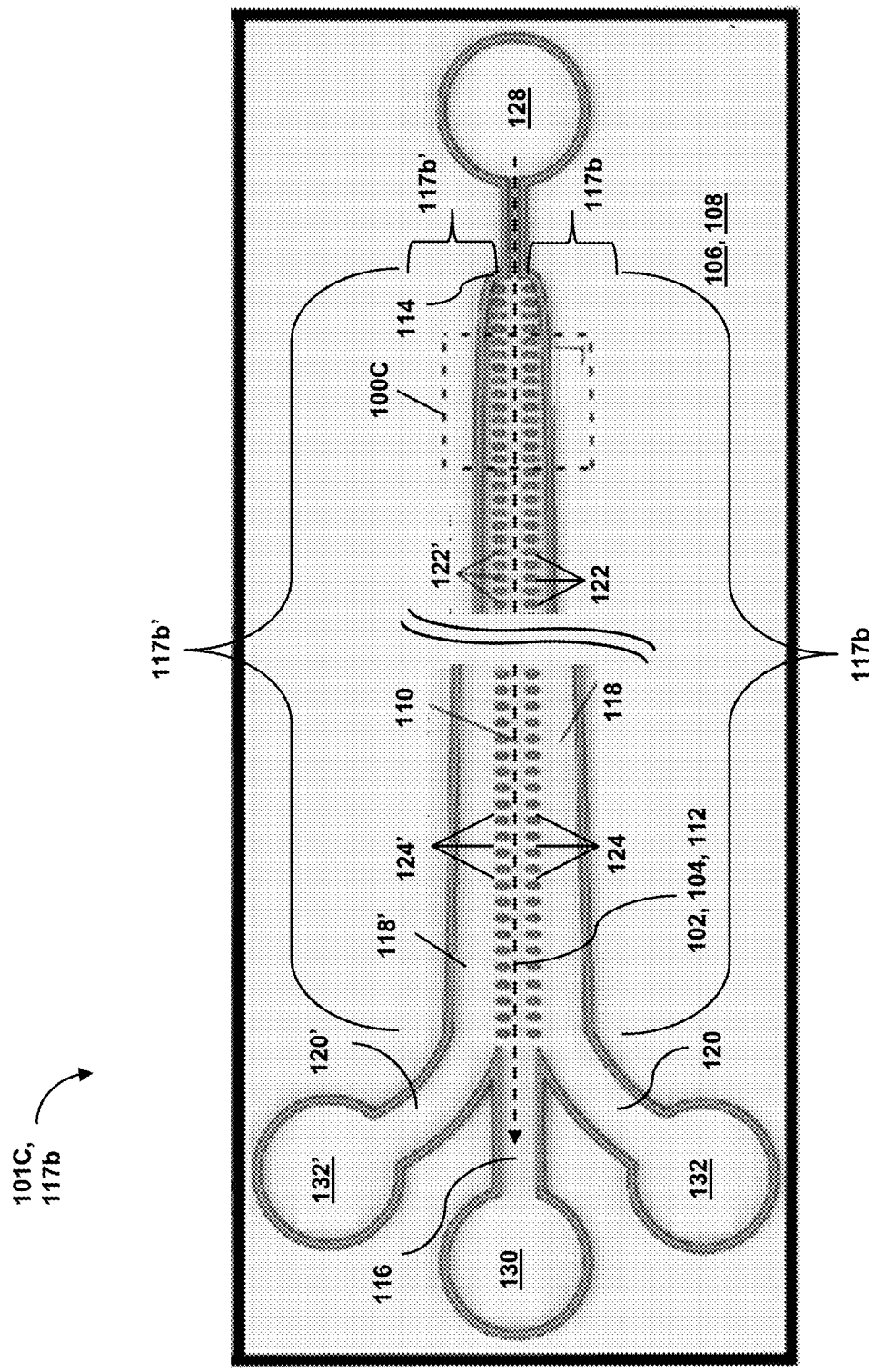
Figure 1D:
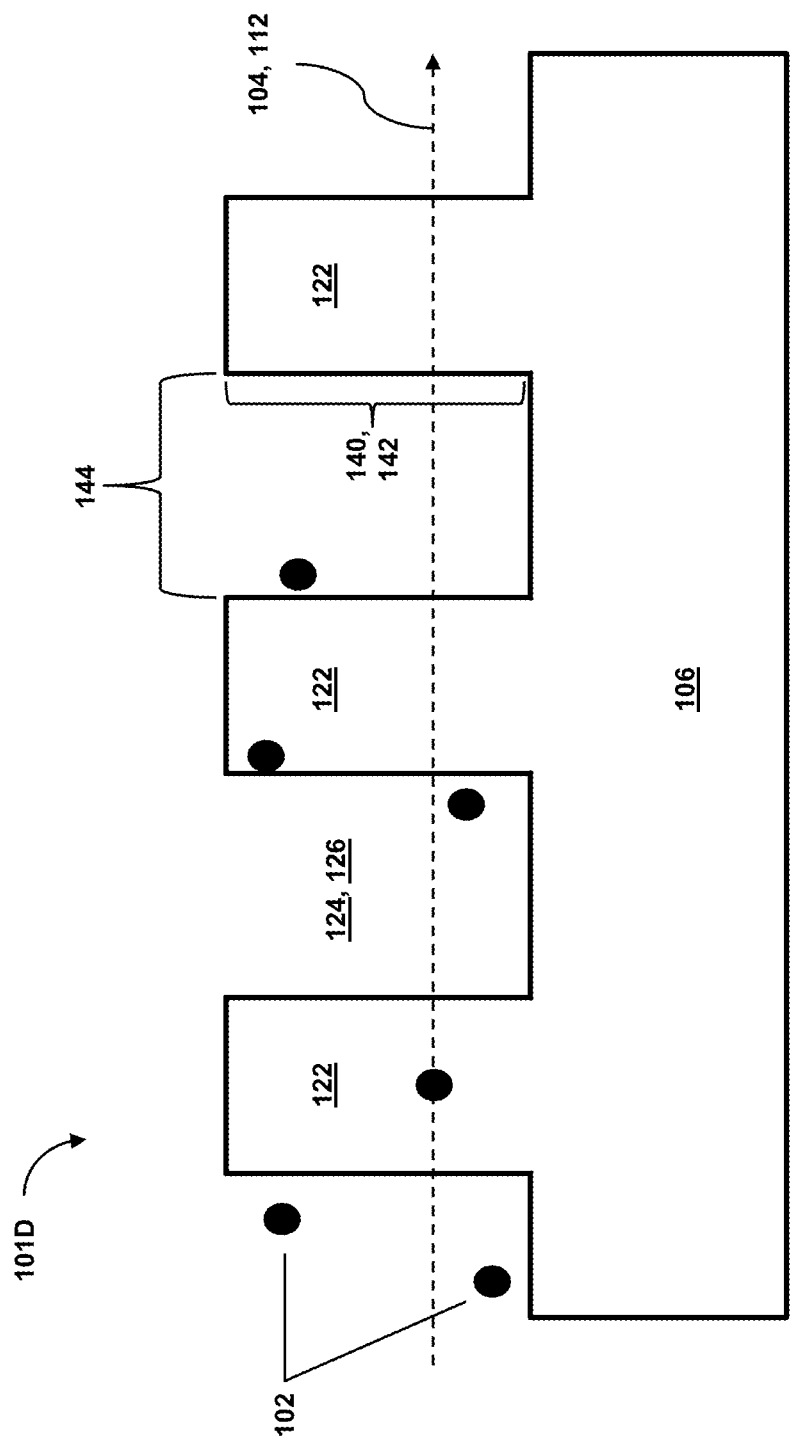
Figure 1E:
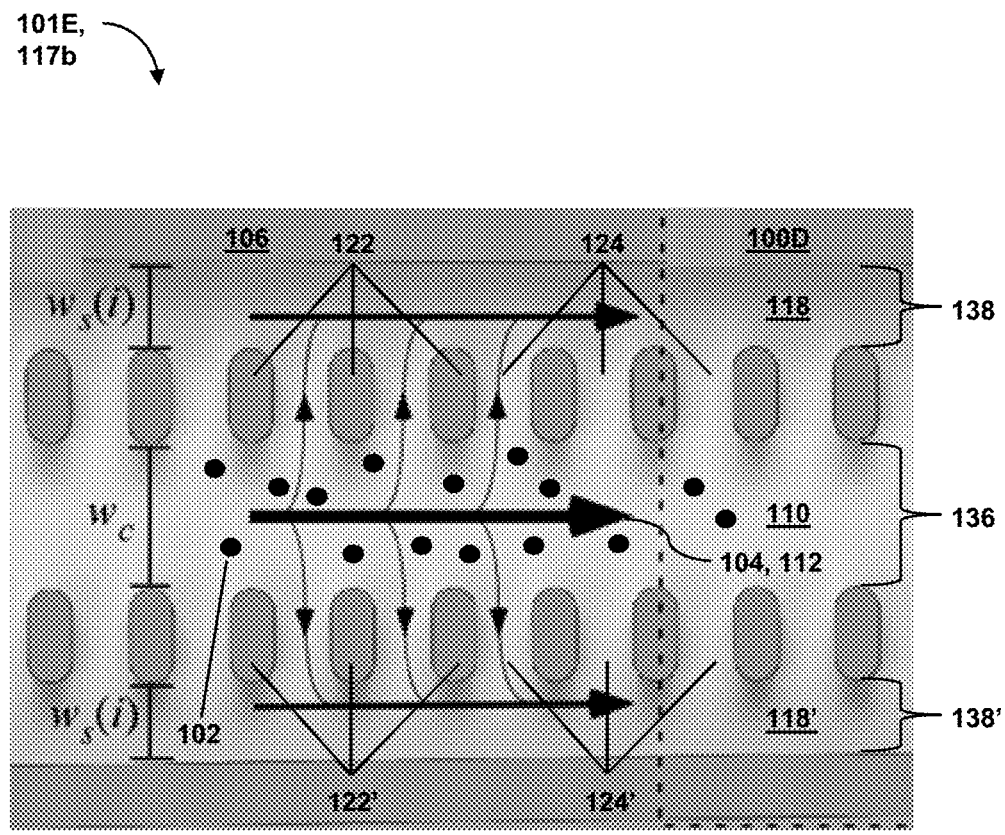
Figure 1F:
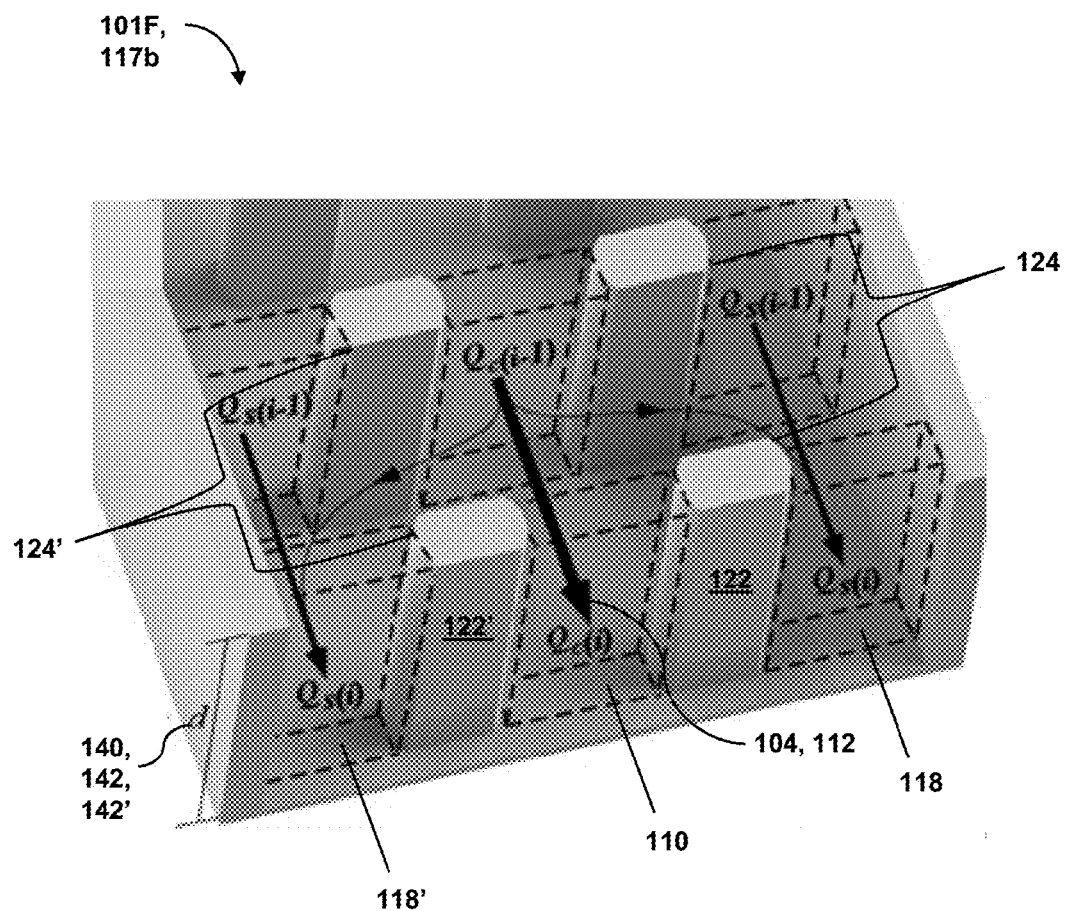
Figure 1G:
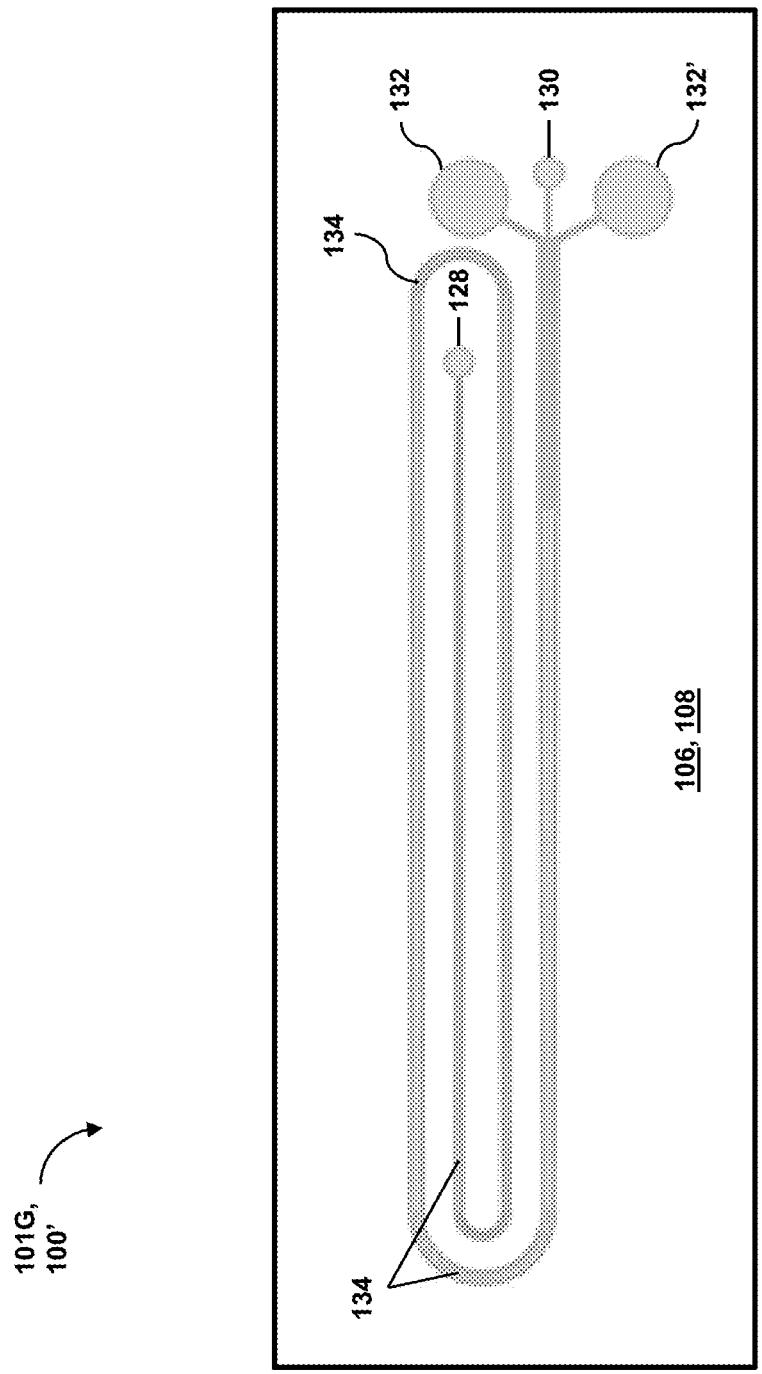
Figure 1H:
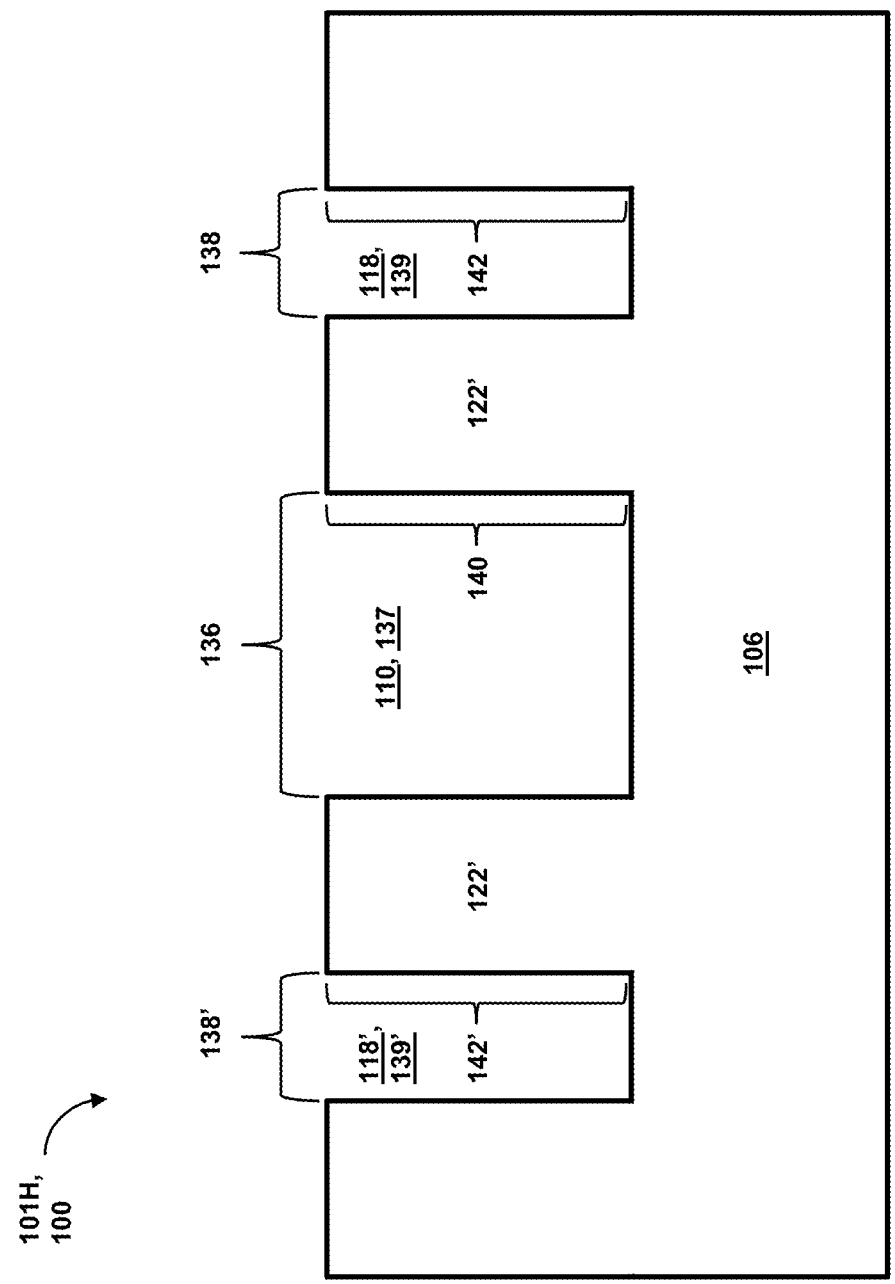

Referring to FIG. 1C, for example, for side channel networks 117, 117', substrate 106 may define two second side channel network portions 117*b*, 117*b'* including at least two side channels 118, 118' adjacent to central channel 110 and at least two pluralities of micro-features 122*b*, 122*b'*. Central channel 110 may be separated from each of side channels 118, 118' by each plurality of micro-features 122*b*, 122*b'*. Pluralities of micro-features 122*b*, 122*b'* may define at least two pluralities of gaps 124*b*, 124*b'*. Pluralities of gaps 124*b*, 124*a'* may be configured to fluidically couple central channel 110 and side channels 118, 118' through pluralities of micro-features 122*b*, 122*b'*.

In various embodiments, corresponding associated features may be indicated by similar feature numbers and similar description exemplification in the FIGS., e.g., micro-features 122 and 122', but distinguished by the prime symbol. For example, substrate 106 may define at least two side channels 118, 118', any description herein referring to at least one side channel 118 or features associated with at least one side channel 118, such as micro-features 122', may correspondingly extend to at least one side channel 118' or corresponding features thereof, such as micro-features 122'. Further, for example, wherein substrate 106 may define at least two side channels 118, 118', each side channel 118, 118' and corresponding associated features thereof may be the same or different. For example, side channel 118 and associated features thereof may be a mirror image with respect to side channel 118' and corresponding associated features thereof across central channel 110 along at least a portion of flow path 112. For example, depths 142 and 142', may be the same or different, e.g., the same. Further, for example, plurality of micro-features 122 and plurality of gaps 124 may have the same or different dimensions, e.g., the same, compared to plurality of micro-features 122' and plurality of gaps 124' along at least a portion of flow path 112. Also, for example, plurality of micro-features 122 and plurality of gaps 124 may be aligned or offset, e.g., aligned, along at least a portion of flow path 112 with respect to plurality of micro-features 122' and plurality of gaps 124'. In various embodiments, corresponding features of central channel 110 may be the same or different, e.g., the same, as corresponding features of side channels 118 and/or 118'. For example, depths 140, 142, and 142' may be the same or different, e.g., the same. It is explicitly contemplated all corresponding associated features indicated herein by similar feature numbers and distinguished by the prime symbol may be the same or different in such manner.

FIG. 1-D is a cross-section view 101D along flow path 112, illustrating various aspects of exemplary CIF device 100. FIG. 1-E is a close-up top view 101E along flow path 112, illustrating various aspects of exemplary CIF device 100 in detail. Plurality of gaps 124 in each CIF module 108 may be characterized by an average gap cross-sectional area 126 parallel to flow path 112. Average gap cross-sectional area 126 may be sized compared to particles 102 of desired size effective to mitigate or eliminate fouling of plurality of gaps 124 by particles 102. For example, gaps of size comparable to the desired size may be fouled or obstructed by particles 102. Selecting average gap cross-sectional area 126 to be large compared to particles 102 may mitigate or eliminate such fouling. Average gap cross-sectional area 126 may be sized compared to particles 102 of desired size effective to mitigate or eliminate steric exclusion of particles 102 by plurality of gaps 124. For example, conventional size exclusion filters function by physically or sterically excluding particles on the basis of size using gaps that are smaller than the particles to be excluded. Selecting average gap cross-sectional area 126 to be large compared to particles 102 may mitigate or eliminate such steric size exclusion, such that gaps 124 may exclude particles 102 based on microfluidic flow behavior in CIF device 100, even though average gap cross-sectional area 126 is large compared to particles 102. Each gap in plurality of gaps 124 in one or more of first side channel network 117*a* and second side channel network 117*b* may be characterized by substantially a same cross-sectional flow area 126 in a plane parallel to flow path 112. Plurality of gaps 124, for example, in one or more of first side channel network 117*a* and second side channel network 117*b* may be substantially equally spaced along flow path 112. Plurality of gaps 124 in each CIF module 108 may include a number of gaps 124 of at least about one or more of: 50, 75, 100, 150, 200, 250, 500, 750, 1,000, 2,500, 5,000, 7,500, 10,000, 50,000, 100,000, 500,000, and 1,000,000, or a range between any two of the preceding values.

In various embodiments, plurality of gaps 124 in one or more of first side channel network 117a and second side channel network 117b may be characterized by an average aspect ratio of a width 144 of each gap 124 parallel to flow path 112 to a depth 142 of each gap 124 in substrate 106. The aspect ratio of width 144 to depth 142 may be of less than about one or more of about: 16:1, 15:1, 10:1, 5:1, 4:1, 3:1, 2:1, 1:1, 1:2, 1:3, 1:4, 1:5, 1:10, 1:15, 1:20, 1:25, and 1:30. Plurality of gaps 124 may be characterized by an average gap depth 142 in substrate 106. Channel 110 may be characterized by a depth 140 in substrate 106. Average gap depth 142 may be a percentage of depth 140 of about one or more of: 5, 6, 7, 8, 9, 10, 15, 20, 25, 30, 40, 50, 60, 70, 80, 90, and 100. Depth 140 may be a value in µm of greater than one or more of about: 5, 10, 15, 20, 25, 30, 35, 40, 45, 50, 75, 100, 125, 150, 200, 250, 300, 400, and 500.

In some embodiments, central channel 110 and plurality of gaps 124 may, in one or more of first side channel network 117a and second side channel network 117b being respectively characterized by a central channel width 136 perpendicular to both flow path 112 and depth 140 of central channel 110. Central channel 110 and plurality of gaps 124 may be characterized by an average gap width 144 parallel to flow path 112. Average gap width 144 may be greater than a percentage of width 136 of one or more of about: 10, 20, 21, 22, 23, 24, 25, 30, 35, 40, 45, and 50.

FIG. 1-F is a close-up perspective view 101F along flow path 112, illustrating various aspects of exemplary CIF device 100. In various embodiments, central channel 110 in each CIF module 108 may be fluidically coupled to an input source 128 through central channel flow input 114. Further, for example, side channel network 117 may be fluidically coupled to input source 128 through plurality of gaps 124 to central channel 110. Central channel 110 may be fluidically coupled to a retentate output reservoir 130. Side channel network 117 may be fluidically coupled to a filtrate output reservoir 132.

Referring to FIG. 1-G, flow path 112 may include one or more turns 134 in substrate 106. Each CIF module 108 may be configured to provide a flow path length in cm of at least one or more of about: 0.1, 0.5, 0.75, 1, 2, 2.5, 5, 7.5, 10, 15, 20, 25, 50, 75, 100, 250, 500, and 1000, or a range between any two of the preceding values.

FIG. 1-H is a cross section view 101H perpendicular to flow path 112, illustrating various aspects of second side channel network portion 117b in exemplary CIF device 100. In several embodiments, second side channel network portion 117b may be characterized by a ratio of a cross-sectional area 139 of side channel 118 to a cross-sectional area 137 of central channel 110. Cross-sectional areas 137, 139 may be perpendicular to flow path 112. The ratio of cross-sectional areas 137, 139 may increase along at least a portion of flow path 112. In some embodiments, the ratio of cross-sectional areas 137, 139 may increase along at least a portion of flow path 112 according to a width 138 of at least one side channel 118 and a width 136 of central channel 110. Each width 136, 138 may be perpendicular to both flow path 112 and a depth 140 of central channel 110 in substrate 106. Flow cross-sectional area 137 may be constant along flow path 112, e.g., along second side channel network portion 117b. Further, for example, flow cross-sectional area 139 of side channel 118 may increase along flow path 112. Each CIF module 108 may be characterized along second side channel network portion 117b by a flow cross-sectional area 137 of central channel 110 perpendicular to flow path 112. Flow cross-sectional area 137 may be, for example, constant, increasing, or decreasing along flow path 112. Further, for example, cross-sectional area 139 of side channel 118 may be constant, increasing, or decreasing along flow path 112.

In several embodiments, CIF device 100 may be characterized at least in part as a function of $f_{gap}$ according to:

$$R_s(i) = \frac{1 - 2f_{gap}}{\frac{1}{R_s(i-1)} + \frac{f_{gap}}{R_c}}, \text{ and} \qquad (\text{eq. 1})$$

$$R(w, d, \mu, L) = \frac{12 \, \mu L}{dw^3}\left[1 - \frac{192w}{d} \cdot \sum_{n=1,3,5,...}^{\infty} \frac{\tanh\left(\frac{n\pi d}{2w}\right)}{(n\pi)^5}\right]^{-1}, \qquad (\text{eq. 2})$$

The symbol $R_c$ may represent flow resistance of central channel 110. The symbol $R_s(i-1)$ may represent flow resistance in a portion of at least one side network 117 between a gap i−1 and a gap i in plurality of gaps 124. The increment symbol i may be increased by 1 for each gap in plurality of gaps 124 along flow path 112. The symbol $R_s(i)$ may represent flow resistance in a portion of at least one side network 117 between the gap i and a gap i+1 in plurality of gaps 124. The symbol $R(w, d, \mu, L)$ may represent resistance of a channel segment in a portion of central channel 110 or at least one side network 117. The symbol w may represent a width corresponding to approximating the channel segment as a rectangular channel. The symbol d may represent a depth corresponding to approximating the channel segment as a rectangular channel. The symbol L may represent a length corresponding to approximating the channel segment as a rectangular channel. The symbol µ may represent a viscosity of the fluid. Each L may correspond to one of plurality of lengths 121a corresponding to plurality of side channel curves 119. Each L may correspond to a length of the channel segment along side channel 118 between a corresponding pair of gaps in plurality of gaps 124.

In various embodiments, CIF device 100 may be characterized as follows. At least a portion of plurality of gaps 124 may be characterized by a flow fraction $f_{gap}$ compared to a volumetric flow $Q_c(i)$ through central channel 110 at the gap i. The flow fraction $f_{gap}$ may be less than one or more of about: 0.01, 0.0075, 0.005, 0.0025, 0.001, 0.00075, 0.0005, 0.00025, 0.0001, 0.000075, 0.00005, 0.000025, and 0.00001. Upon conducting a microfluidic flow using a mixture of 1% w/w 4 µm polystyrene microbeads in water at a temperature of 25° C. and a flow pressure of 2 PSI through each CIF module 108, flow fraction $f_{gap}$ may be an average characterized by a percent standard deviation among plurality of gaps 124 of less than about ±1, 2.5, 5, 7.5, 10, 15, and 20. Each CIF module 108 may be configured, upon conducting the microfluidic flow using a mixture of 1% w/w 4 µm polystyrene microbeads in water at a temperature of 25° C. and a flow pressure of 2 PSI, to concentrate particles 102 of the desired size in microfluidic flow 104. The concentration, from a starting particle concentration at central channel flow input 114 to a final concentration at central channel flow output 116 may include a concentration factor of one or more of about: 1.5:1, 2:1, 2.5:1, 3:1, 3.5:1, 4:1, 5:1, 7,5:1, 10:1, 15:1, 20:1, 25:1, 50:1, 75:1, 100:1, 125:1, 150:1, 200:1, and 250:1. Each CIF module 108 may be configured to retain a percentage of particles 102 in microfluidic flow 104. The percentage of particles 102 retained may be at least one or more of about: 50, 55, 60, 65, 70, 75, 80, 85, 90, 95, 97.5, 99, and 100.

In various embodiments, the desired size of particles 102 may be characterized by an effective average diameter in μm of greater than one or more of about: 0.5, 1, 1.2, 1.4, 1.6, 1.8, 2, 2.5, 3, 3.5, 4, 4.5, 5, 7.5, 10, 15, 20, 25, 50, 75, 100, 125, and 150. Plurality of gaps 124 may be configured in each CIF module 108 with an average gap cross-sectional area 126 parallel to flow path 112. Average gap cross-sectional area 126 may be greater than the desired size of particles 102 to be separated from the microfluidic flow. Average gap cross-sectional area 126 may be greater than the desired size of particles 102 by a factor of one or more of about: 2:1, 3:1, 4:1, 5:1, 7.5:1, 10:1, 15:1, and 20:1.

In various embodiments, particles 102 may include one or more of: red blood cells, platelets, white blood cells, circulating tumor cells, stem cells, effete stored erythrocytes, T-cells derived from autologous T-cell expansion, organic microparticles, inorganic microparticles, organometallic microparticles, metallic microparticles, aerosol particles, bacteria, yeast, fungi, algae, viruses, micro-invertebrates or eggs thereof, pollen, cell or tissue fragments, cell clusters, cellular debris (e.g., cellular debris associated with DNA or RNA purification), bioreactor-produced cells or particulates, proteins, protein aggregates, prions, vesicles, liposomes, precipitates (e.g., precipitates from blood or a blood fraction, industrial process precipitates, wastewater precipitates, and the like), particulates or cells from fermented foods (e.g., particulates or cells from fermented beverages), macromolecules, macromolecular aggregates, DNA, organelles, spores, stem cells, bubbles, droplets, and exosomes. Microfluidic flow 104 may include particles 102 in a fluid. The fluid may include one or more of: whole blood or a fraction thereof; amniotic fluid; umbilical cord blood; bile; cerebrospinal fluid; skin cells; exudate; feces; gastric fluid; lymph; milk; mucus; peritoneal fluid; plasma; pleural fluid; pus; saliva; sebum; semen; sweat; synovial fluid; tears; urine; water; buffer; groundwater; seawater; rainwater; sap; animal tissue homogenate, extract, or pressing; plant tissue homogenate, extract, or pressing; wastewater; an industrial process fluid or fluid product; fermentation broth; crystallization or precipitation fluid; a food or food process intermediate (e.g., a fermented beverage); oil; inorganic solvent; organic solvent; ionic solvent; honey; syrup; lymphatic fluid; serum; and lysate.

In various embodiments, CIF module 108 may be configured capable of conducting the microfluidic flow as one or more of: a gravitationally-directed flow, a vacuum directed flow, an electroosmotic directed flow, an electrokinetic directed flow, a mechanically pumped flow, e.g., using a syringe pump; and the like. Each CIF module 108 may be configured such that a volumetric flow of central channel flow output 116 and a volumetric flow of at least one side channel output 120 are substantially equal.

Figure 2A:
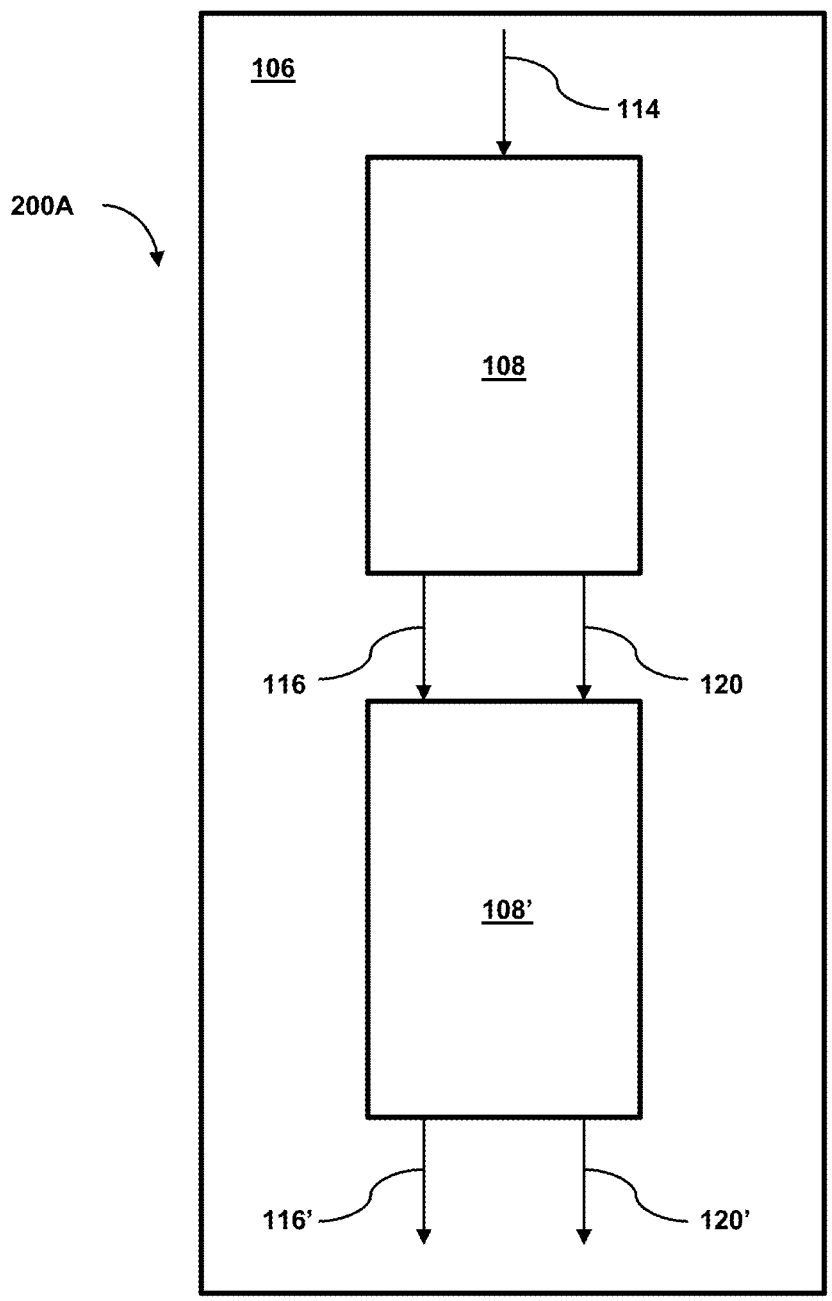
FIG. 2-A is a block diagram of a CIF device including two CIF modules fluidically coupled in series.
Figure 2B:
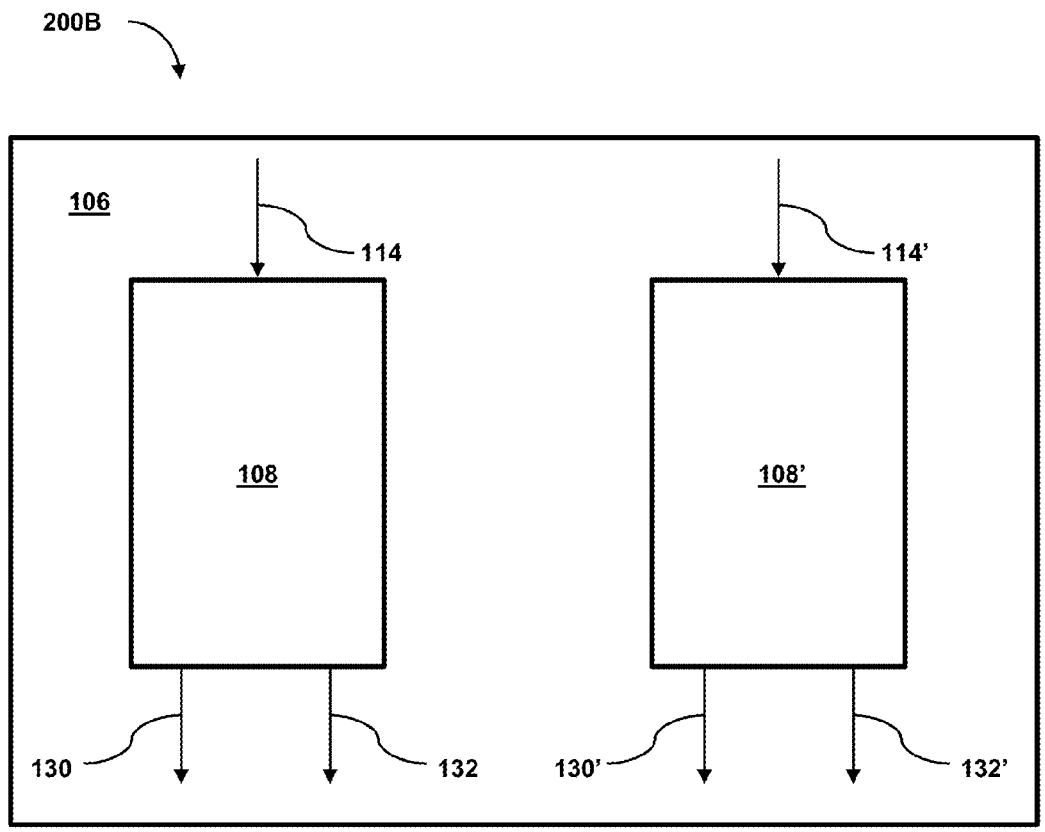

In several embodiments, substrate 106 may include two or more of CIF modules 108, 108'. Substrate 106 may include an array of two or more CIF modules 108, 108' fluidically coupled in series or in parallel. For example, substrate 106 may include an array 200A of the two or more CIF modules 108, 108' fluidically coupled in series, as depicted in FIG. 2A. Substrate 106 may include an array 200B of two or more CIF modules 108, 108' fluidically coupled in parallel, as depicted in FIG. 2-B. The arrangements and flows depicted in FIGS. 2-A and 2-B are merely exemplary, and other arrangements and flows are contemplated.

Figure 3:
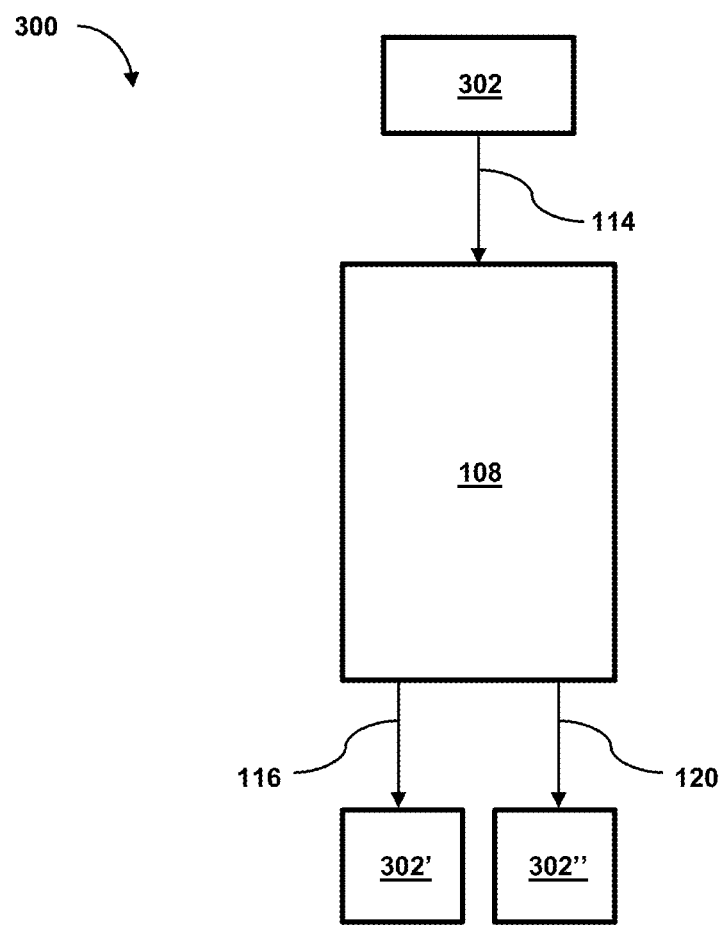
FIG. 3 is a block diagram of a CIF device including at least one additional separation device.

CIF device 100 may further include at least one additional separation device 302 as depicted in FIG. 3. Separation devices 302, 302', 302" may be fluidically coupled to one or more of: central channel flow input 114, central channel flow output 116, and at least one side channel flow output 120. Additional separation devices 302, 302', 302" may include one or more of: a filter, a centrifuge, an electrophoresis device, a chromatography column, a fluid evaporator, a sedimentation device, a deterministic lateral displacement device, a plasma skimmer, a margination device, a magnetic separator, an ultrasound focusing device, a density gradient separator, and the like.

Substrate 106 may include one or more of: a glass, a polymer, a metal, a ceramic, and a semiconductor. Substrate 106 may include a thermoplastic polymer, e.g., polycarbonate, or an elastomeric rubber, e.g., polydimethylsiloxane. CIF device 100 may be configured to be one or more of: disposable, sterile, and sterilizable.

Figure 4:
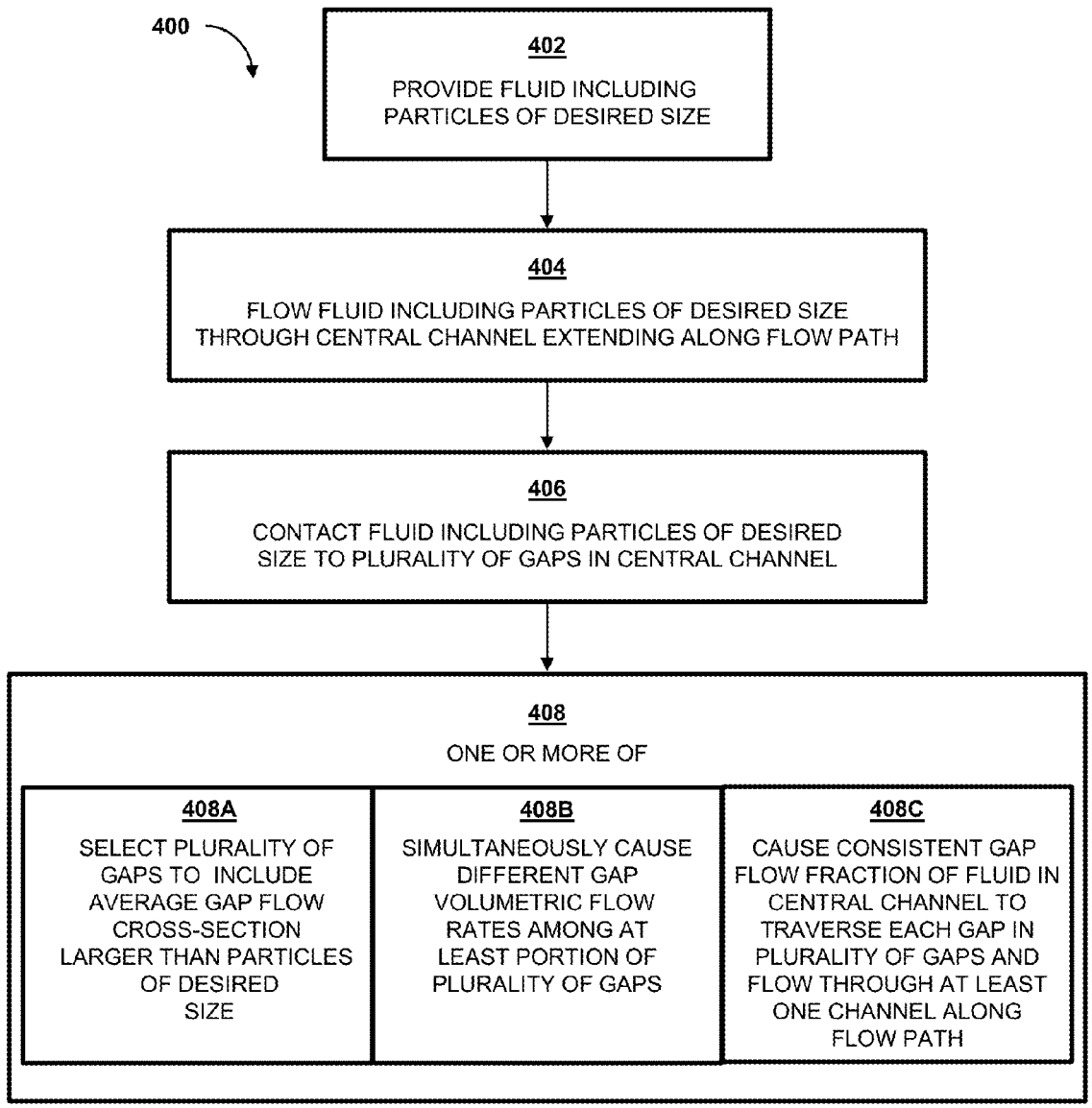
FIG. 4 is a flow diagram depicting an exemplary method for controlled incremental filtration.

FIG. 4 is a flow diagram illustrating a method 400 for controlled incremental filtration. In various embodiments, method 400 may concentrate particles of a desired size in a fluid. Method 400 may include 402 providing the fluid including the particles of the desired size. It is to be understood that "the fluid including the particles of the desired size" may include fluids for testing, e.g., to determine whether significant amounts of the particles of the desired size are present. Method 400 may include 404 flowing the fluid comprising the particles of the desired size along a flow path through a central channel. The central channel may include a plurality of gaps that fluidically couple the central channel to at least one adjacent side channel network. Method 400 may include 406 decreasing flow resistance along at least a portion of the flow path effective to modulate the concentration of particles by contacting the fluid comprising the particles of the desired size to the plurality of gaps. Method 400 may include 408, 408A selecting the plurality of gaps including an average flow cross-section larger than the particles of the desired size. Method 400 may include 408, 408B causing different gap volumetric flow rates among at least a portion of the plurality of gaps. Method 400 may include 408, 408C causing a consistent flow fraction $f_{gap}$ in the central channel to traverse each gap in the plurality of gaps and flow through the at least one side channel network along the flow path.

Method 400 may include providing the at least one side channel network. The at least one side channel network may include a first channel network portion. The first channel network portion may include a plurality of side channel curves adjacent to the central channel. The plurality of side channel curves may be characterized by decreasing length along the flow path effective to decrease the flow resistance. The at least one side channel network may include a second side channel network portion. The second side channel network portion may include a side channel adjacent to the central channel. The side channel may be characterized by an increasing flow cross-section along the flow path effective to cause one or more of: the consistent flow fraction $f_{gap}$ and the plurality of different gap volumetric flow rates. The method may include flowing the fluid through the first side channel network portion followed by the second side channel network portion in sequence along the flow path.

In some embodiments, method 400 may include selecting the plurality of gaps including an average gap cross-sectional area larger compared to the particles of desired size. Compared to gaps smaller than the particles, the larger average gap cross-sectional area larger may be effective for mitigating or eliminating fouling of the plurality of gaps by the particles. The larger average gap cross-sectional area larger may also be effective for mitigating or eliminating steric exclusion of the particles by the plurality of gaps.

In several embodiments, method 400 may include providing an average aspect ratio of a width of each gap along the flow path to a depth of each gap of less than one or more of: 16:1, 15:1, 10:1, 5:1, 4:1, 3:1, 2:1, 1:1, 1:2, 1:3, 1:4, 1:5, 1:10, 1:15, 1:20, 1:25, and 1:30. The central channel may include a depth in μm of greater than one or more of about: 5, 10, 15, 20, 25, 30, 35, 40, 45, 50, 75, 100, 125, 150, 200, 250, 300, 400, and 500. An average depth of the plurality of gaps may be greater than a depth of the central channel by a percentage of one or more of about: 5, 6, 7, 8, 9, 10, 15, 20, 25, 30, 40, 50, 60, 70, 80, 90, and 100. An average gap width along the flow path of the plurality of gaps may be greater than a width of the central channel by a percentage of one or more of about: 20, 21, 22, 23, 24, 25, 30, 40, 50, 60, 70, 80, 90, and 100. The average gap flow cross-section may be larger than the particles of the desired size by a factor of one or more of about: 2:1, 3:1, 4:1, 5:1, 7.5:1, 10:1, 15:1, and 20:1.

In various embodiments, method 400 may include providing two side channel networks adjacent to the central channel along the flow path. The method may include providing a flow path length in cm of at least one or more of about: 0.1, 0.5, 0.75, 1, 2, 2.5, 5, 7.5, 10, 15, 20, 25, 50, 75, 100, 250, 500, and 1000. The method may include providing the plurality of gaps for each at least one side channel network including a number of gaps of at least about one or more of: 50, 75, 100, 150, 200, 250, 500, 750, 1,000, 2,500, 5,000, 7,500, 10,000, 50,000, 100,000, 500,000, and 1,000,000. The method may include increasing a ratio along the flow path of a cross-sectional area of the at least one side channel to a cross-sectional area of the central channel. The ratio of the cross-sectional area of the at least one side channel to the cross-sectional area of the central channel may be increased along the flow path according to a width of the at least one side channel and a width of the central channel. The method may include increasing the ratio along the flow path, including holding the cross-sectional area of the central channel constant along the flow path and increasing the cross-sectional area of the at least one side channel along the flow path. The method may include increasing the ratio along the flow path comprising decreasing the cross-sectional area of the central channel constant along the flow path and maintaining or increasing the cross-sectional area of the at least one side channel along the flow path. The method may include increasing the ratio along the flow path including maintaining, increasing, or decreasing the cross-sectional area of the central channel along the flow path. The method may include increasing the ratio along the flow path including maintaining, increasing, or decreasing the cross-sectional area of the at least one side channel along the flow path.

In various embodiments, the method may include increasing a ratio along the flow path of a fluidic resistance of the at least one side channel to a fluidic resistance of the central channel.

In some embodiments, method 400 may include flowing the fluid characterized at least in part as a function of $f_{gap}$ according to one or more of:

$$R_s(i) = \frac{1 - 2f_{gap}}{\frac{1}{R_s(i-1)} + \frac{f_{gap}}{R_c}}, \text{ and} \quad \text{(eq. 1)}$$

$$R(w, d, \mu, L) = \frac{12\,\mu L}{dw^3}\left[1 - \frac{192w}{d} \cdot \sum_{n=1,3,5,\ldots}^{\infty} \frac{\tanh\left(\frac{n\pi d}{2w}\right)}{(n\pi)^5}\right]^{-1}, \quad \text{(eq. 2)}$$

The symbol $R_c$ may represent flow resistance of central channel 110. The symbol $R_s(i-1)$ may represent flow resistance in a portion of at least one side network 117 between a gap i−1 and a gap i in the plurality of gaps. The increment symbol i may be increased by 1 for each gap in the plurality of gaps along the flow path. The symbol $R_s(i)$ may represent flow resistance in a portion of at least one side network between the gap i and a gap i+1 in the plurality of gaps. The symbol $R(w, d, \mu, L)$ may represent resistance of a channel segment in a portion of the central channel or at least one side network. The symbol w may represent a width corresponding to approximating the channel segment as a rectangular channel. The symbol d may represent a depth corresponding to approximating the channel segment as a rectangular channel. The symbol L may represent a length corresponding to approximating the channel segment as a rectangular channel. The symbol μ may represent a viscosity of the fluid.

In some embodiments of method 400, the flow fraction $f_{gap}$ at a gap i may be a volumetric flow $Q_c(i)$ through the central channel at the gap i of less than one or more of about: 0.01, 0.0075, 0.005, 0.0025, 0.001, 0.00075, 0.0005, 0.00025, 0.0001, 0.000075, 0.00005, 0.000025, and 0.00001. The method may include causing the flow fraction $f_{gap}$ to have a percent standard deviation among the plurality of gaps of less than about one or more of: ±1, 2.5, 5, 7.5, 10, 15, and 20. The method may include providing each gap in the plurality of gaps with substantially the same flow cross-section. The method may include providing the plurality of gaps substantially equally spaced along the flow path.

In various embodiments, method 400 may include conducting at least one additional separation. The at least one additional separation may be conducted before or after flowing the fluid including the particles of the desired size through the central channel. The additional separation may include one or more of: filtering, centrifuging, electrophoresis, chromatography, fluid evaporation, sedimentation, deterministic lateral displacement, plasma skimming, margination, magnetic separation, ultrasound focusing device, density gradient separation, and the like.

In some embodiments, method 400 may include concentrating the particles of the desired size in the fluid in the central channel by a concentration factor of one or more of about: 1.5:1, 2:1, 2.5:1, 3:1, 3.5:1, 4:1, 5:1, 7,5:1, 10:1, 15:1, 20:1, 25:1, 50:1, 75:1, 100:1, 125:1, 150:1, 200:1, and 250:1. The method may include retaining a percentage of the particles of the desired size in the fluid in the central channel of at least one or more of about: 50, 55, 60, 65, 70, 75, 80, 85, 90, 95, 97.5, 99, and 100.

In several embodiments of method 400, the desired size of the particles may be characterized by an effective average diameter in μm of greater than one or more of about: 0.5, 1, 1.2, 1.4, 1.6, 1.8, 2, 2.5, 3, 3.5, 4, 4.5, 5, 7.5, 10, 15, 20, 25, 50, 75, 100, 125, and 150. The particles may include one or more of: red blood cells, platelets, white blood cells, circulating tumor cells, stem cells, effete stored erythrocytes, T-cells derived from autologous T-cell expansion, organic microparticles, inorganic microparticles, organometallic microparticles, metallic microparticles, aerosol particles, bacteria, yeast, fungi, algae, viruses, micro-invertebrates or eggs thereof, pollen, cell or tissue fragments, cell clusters, cellular debris (e.g., cellular debris associated with DNA or RNA purification), bioreactor-produced cells or particulates, proteins, protein aggregates, prions, vesicles, liposomes, precipitates (e.g., precipitates from blood or a blood fraction, industrial process precipitates, wastewater precipitates, and the like), particulates or cells from fermented foods (e.g., particulates or cells from fermented beverages), macromolecules, macromolecular aggregates, DNA, organelles, spores, stem cells, bubbles, droplets, exosomes, and the like. The fluid may include one or more of: whole blood or a fraction thereof; amniotic fluid; umbilical cord blood; bile; cerebrospinal fluid; skin cells; exudate; feces; gastric fluid; lymph; milk; mucus; peritoneal fluid; plasma; pleural fluid; pus; saliva; sebum; semen; sweat; synovial fluid; tears; urine; water; buffer; groundwater; seawater; rainwater; sap; animal tissue homogenate, extract, or pressing; plant tissue homogenate, extract, or pressing; wastewater; an industrial process fluid or fluid product; fermentation broth; crystallization or precipitation fluid; a food or food process intermediate (e.g., a fermented beverage); oil; inorganic solvent; organic solvent; ionic solvent; honey; syrup; lymphatic fluid; serum; lysate; and the like.

In various embodiments, method 400 may include collecting one or more of a retentate fraction from the central channel and a filtrate fraction from the at least one side network. The method may include collecting a fraction of the fluid comprising an increased or a decreased concentration of the particles of the desired size. The method may include flowing the fluid including conducting one or more of: gravitational flow, vacuum flow, electroosmotic flow, electrokinetic flow, mechanically pumped flow (e.g., using a syringe pump), and the like. The method may include providing substantially equal volumetric flows of the fluid at an output of the central channel flow and an output of the at least one side channel. The method may include operating two or more instances of the method in one or more of: parallel operation and serial operation. The method may include flowing the fluid including the particles of the desired size by flowing along one or more turns in the flow path.

Figure 5:
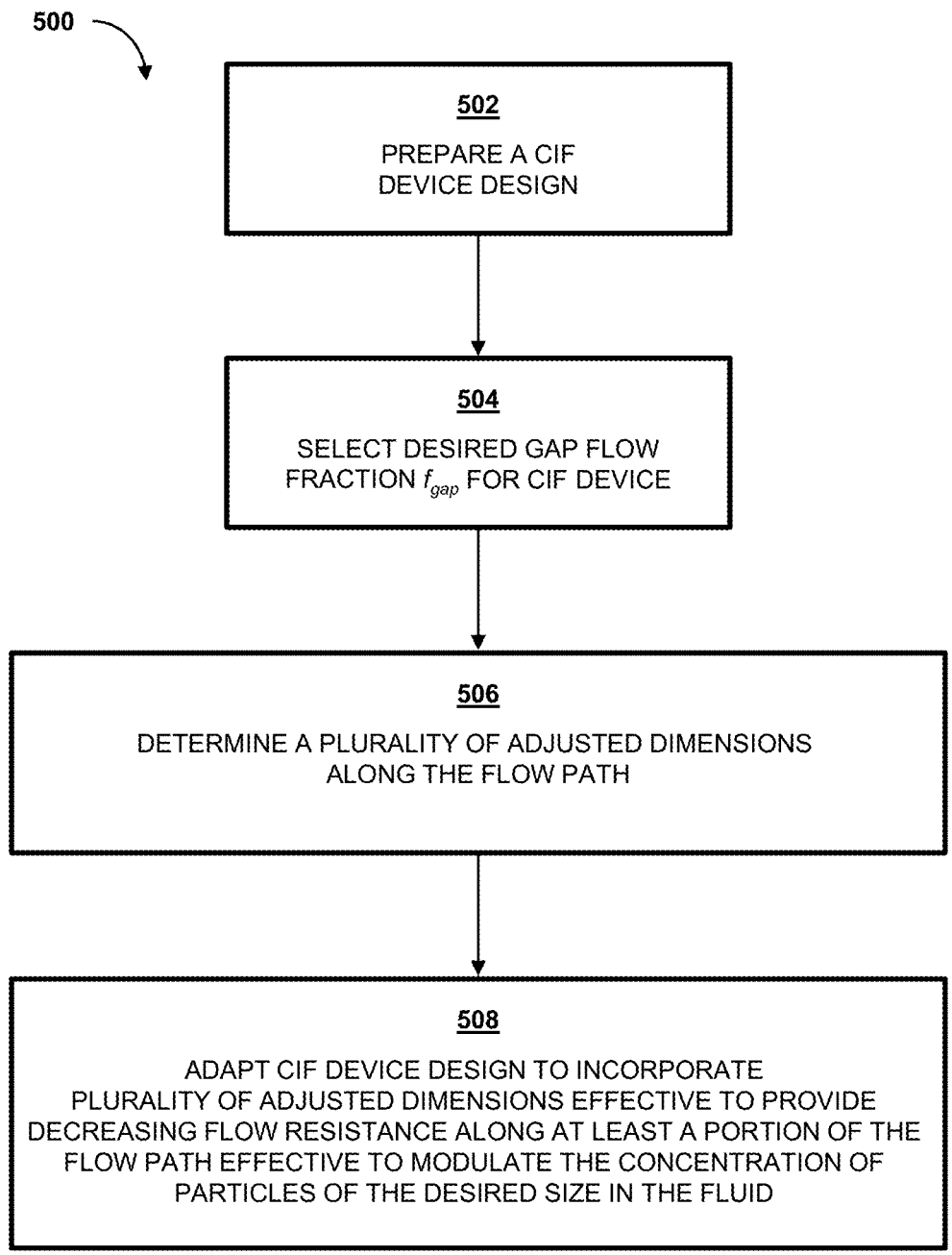
FIG. 5 is a flow diagram depicting an exemplary method for designing a CIF device.

FIG. 5 is a flow diagram illustrating a method 500 for designing a CIF device. The CIF device may modulate a concentration of particles of a desired size in a fluid. Method 500 may include 502 preparing a design for a CIF device. The CIF device design may include a central channel. The central channel may extend along a flow path between a central channel flow input and a central channel flow output. The CIF device design may include at least one side channel adjacent to the central channel. The at least one side channel may extend along the flow path to at least one side channel output. The central channel may be separated from the at least one side channel by a plurality of micro-features. The plurality of micro-features may define a plurality of gaps i. The plurality of gaps may be configured to fluidically couple the central channel and the at least one side channel through the plurality of micro-features. Method 500 may include 504 selecting a desired flow fraction $f_{gap}$ for the CIF device. Method 500 may include 506 determining a plurality of adjusted dimensions along the flow path. Method 500 may include 508 adapting the CIF device design to incorporate the plurality of the adjusted dimensions. Incorporating the adjusted dimensions may be effective to provide a decreasing flow resistance along at least a portion of the flow path effective to modulate the concentration of particles of the desired size in the fluid for the design for the CIF device.

In various embodiments of method 500, the adjusted dimensions along the flow path may include, in a first side network portion, a decreasing length of each of a plurality of side channel curves. The plurality of side channel curves may be adjacent to the central channel in the first side channel network portion. The adjusted dimensions along the flow path may include, in a second side network portion, an increasing ratio of a cross-sectional area of at least one side channel to a cross-sectional area of the central channel. The at least one side channel may be adjacent to the central channel in the second side network portion.

In some embodiments, method 500 may include providing one or more test CIF devices. Each of the test CIF devices may be characterized by a corresponding test flow fraction $f_{gap}$. The method may include flowing the particles of the desired size in the fluid through the one or more test CIF devices. The method may include determining the desired flow fraction $f_{gap}$ for the design for the CIF device based on each corresponding test flow fraction $f_{gap}$ in the one or more test CIF devices.

In several embodiments, method 500 may include determining the plurality of adjusted dimensions by determining a central channel flow resistance $R_c$. The method may include determining a first side channel segment flow resistance corresponding to a first side channel segment between a first pair of adjacent gaps in the plurality of gaps along the flow path. The first flow resistance may be determined according to a first functional relationship between: a viscosity of the fluid; a first effective side channel width w and a first effective channel depth d corresponding to a first cross-sectional area at the first side channel segment; and a length L of the first side channel segment. The method may include determining a second side channel segment flow resistance corresponding to a second side channel segment between a second pair of adjacent gaps in the plurality of gaps along the flow path. The second side channel segment may be located immediately downstream of the first side channel segment. The second side channel segment flow resistance may be determined according to a second functional relationship between: the central channel flow resistance, the first side channel segment flow resistance, and the desired flow fraction $f_{gap}$ for the CIF device. The method may include recalculating the first functional relationship using one or more adjusted dimensions comprising one or more of: a second effective side channel width w; a second effective channel depth d; and a second side channel length L. The one or more adjusted dimensions may be effective to cause the first side channel segment flow resistance according to the first functional relationship to equal the second side channel segment flow resistance. The one or more adjusted dimensions may be effective to cause the second side channel segment flow resistance according to the second functional relationship to be lower than the first side channel segment flow resistance by an amount determined according to the second functional relationship. The method may include conducting one or more of the preceding steps for a plurality of iterations to calculate the plurality of the adjusted dimensions.

In various embodiments, method 500 may include holding the cross-sectional area of the central channel constant along the flow path and each effective channel depth d such that the ratio increases according to the one or more of: increasing the second effective side channel width w; and decreasing the second side channel length L. The side channel network may include a plurality of side channel curves characterized by a plurality of side channel curve lengths. The plurality of side channel curves may be adjacent to the central channel. The method may include progressively decreasing the plurality of side channel curve lengths along the flow path. The side channel network may include a side channel adjacent to the central channel. The method may include progressively increasing a width of the side channel along the flow path. The method may include, for each functional relationship, approximating each channel segment as a rectangular channel. The method may include recalculating the first functional relationship by numerically solving the first functional relationship for the one or more adjusted dimensions.

In some embodiments of method 500, the first functional relationship may be represented by:

$$R(w, d, \mu, L) = \frac{12\,\mu L}{dw^3}\left[1 - \frac{192w}{d}\cdot\sum_{n=1,3,5,\ldots}^{\infty}\frac{\tanh\left(\frac{n\pi d}{2w}\right)}{(n\pi)^5}\right]^{-1}.$$

The second functional relationship being represented by:

$$R_s(i) = \frac{1 - 2f_{gap}}{\frac{1}{R_s(i-1)} + \frac{f_{gap}}{R_c}}$$

The symbol $R_s(i-1)$ may represent the first side channel segment flow resistance. The symbol $R_s(i)$ may represent the second side channel segment flow resistance.

In several embodiments, method 500 may include selecting the plurality of gaps in the design for the CIF device characterized by an average gap cross-sectional area parallel to the central channel along the flow path. The average gap cross-sectional area may be selected larger compared to the particles of desired size effective for mitigating or eliminating fouling of the plurality of gaps by the particles. The average gap cross-sectional area may be selected larger compared to the particles of desired size effective for mitigating or eliminating steric exclusion of the particles by the plurality of gaps.

In various embodiments of method 500, the design for the CIF device may include at least two side channel networks adjacent to the central channel and at least two corresponding pluralities of the micro-features. The central channel may be separated from each of the at least two side channels by each plurality of micro-features. The at least two pluralities of micro-features may define at least two pluralities of gaps. The at least two pluralities of gaps may be configured to fluidically couple the central channel and the at least two side channels through the at least two pluralities of the micro-features. The design for the CIF device may include one or more turns in the flow path.

In some embodiments of method 500, each gap in the plurality of gaps in the design for the CIF device may be characterized by substantially the same cross-sectional flow area in a plane parallel to the flow path. For example, the plurality of gaps in the design for the CIF device may be substantially equally spaced along the flow path. The design for the CIF device may be configured to provide a flow path length in cm of at least one or more of about: 0.1, 0.5, 0.75, 1, 2, 2.5, 5, 7.5, 10, 15, 20, 25, 50, 75, 100, 250, 500, and 1000. The plurality of gaps for the design for the CIF device may include a number of gaps of at least about one or more of: 50, 75, 100, 150, 200, 250, 500, 750, 1,000, 2,500, 5,000, 7,500, 10,000, 50,000, 100,000, 500,000, and 1,000,000. The design for the CIF device may be characterized by a cross-sectional area of the central channel perpendicular to the flow path. The cross-sectional area of the central channel may be constant, increasing, or decreasing along the flow path. The design for the CIF device may be characterized by a cross-sectional area of the at least one side channel perpendicular to the flow path. The cross-sectional area of the at least one side channel may be constant, increasing, or decreasing along the flow path. The plurality of gaps in the design for the CIF device may be characterized by an average aspect ratio of a width of each gap parallel to the flow path to a depth of each gap of less than about one or more of about: 16:1, 15:1, 10:1, 5:1, 4:1, 3:1, 2:1, 1:1, 1:2, 1:3, 1:4, 1:5, 1:10, 1:15, 1:20, 1:25, and 1:30. The plurality of gaps in the design for the CIF device may be characterized by an average gap depth. The average gap depth may be greater than a percentage of a depth of the central channel of about one or more of: 5, 6, 7, 8, 9, 10, 15, 20, 25, 30, 40, 50, 60, 70, 80, 90, and 100. The central channel may be characterized by a depth in μm of greater than one or more of about: 5, 10, 15, 20, 25, 30, 35, 40, 45, 50, 75, 100, 125, 150, 200, 250, 300, 400, and 500.

In several embodiments of method 500, the central channel and the plurality of gaps may be respectively characterized by (1) a central channel width perpendicular to both the flow path and the depth of the central channel in the substrate and (2) an average gap width parallel to the flow path. The average gap width may be greater than a percentage of the width of the central channel of one or more of about: 10, 20, 21, 22, 23, 24, 25, 30, 35, 40, 45, and 50. The design for the CIF device may be configured such that compared to a volumetric flow $Q_c(i)$ through the central channel at a gap i, the desired flow fraction $f_{gap}$ is selected to be less than one or more of about: 0.01, 0.0075, 0.005, 0.0025, 0.001, 0.00075, 0.0005, 0.00025, 0.0001, 0.000075, 0.00005, 0.000025, and 0.00001. The design for the CIF device may be configured effective to provide a realized flow fraction $f_{gap}$ among the plurality of gaps characterized by a percentage standard deviation of less than about ±1, 2.5, 5, 7.5, 10, 15, and 20. The design for the CIF device may be configured effective to concentrate the particles of the desired size in the microfluidic fluid flow from a starting particle concentration at the central channel flow input to a final concentration at the central channel flow output by a concentration factor of one or more of about: 1.5:1, 2:1, 2.5:1, 3:1, 3.5:1, 4:1, 5:1, 7,5:1, 10:1, 15:1, 20:1, 25:1, 50:1, 75:1, 100:1, 125:1, 150:1, 200:1, and 250:1. The design for the CIF device may be configured effective to retain a percentage of the particles in the microfluidic fluid flow, the percentage of particles retained being at least one or more of about: 50, 55, 60, 65, 70, 75, 80, 85, 90, 95, 97.5, 99, and 100.

In various embodiments of method 500, the plurality of gaps may be configured with an average gap cross-sectional area parallel to the flow path. The average gap cross-sectional area may be greater than the desired size of the particles. The desired size of the particles may be selected with an effective average diameter in μm of greater than one or more of about: 0.5, 1, 1.2, 1.4, 1.6, 1.8, 2, 2.5, 3, 3.5, 4, 4.5, 5, 7.5, 10, 15, 20, 25, 50, 75, 100, 125, and 150. The average gap cross-sectional area may be greater than the desired size of the particles by a factor of one or more of about: 2:1, 3:1, 4:1, 5:1, 7.5:1, 10:1, 15:1, and 20:1. The particles may include one or more of: red blood cells, platelets, white blood cells, circulating tumor cells, stem cells, effete stored erythrocytes, T-cells derived from autologous T-cell expansion, organic microparticles, inorganic microparticles, organometallic microparticles, metallic microparticles, aerosol particles, bacteria, yeast, fungi, algae, viruses, micro-invertebrates or eggs thereof, pollen, cell or tissue fragments, cell clusters, cellular debris (e.g., cellular debris associated with DNA or RNA purification), bioreactor-produced cells or particulates, proteins, protein aggregates, prions, vesicles, liposomes, precipitates (e.g., precipitates from blood or a blood fraction, industrial process precipitates, wastewater precipitates, and the like), particulates or cells from fermented foods (e.g., particulates or cells from fermented beverages), macromolecules, macromolecular aggregates, DNA, organelles, spores, stem cells, bubbles, droplets, exosomes, and the like. The fluid may include one or more of: whole blood or a fraction thereof; amniotic fluid; umbilical cord blood; bile; cerebrospinal fluid; skin cells; exudate; feces; gastric fluid; lymph; milk; mucus; peritoneal fluid; plasma; pleural fluid; pus; saliva; sebum; semen; sweat; synovial fluid; tears; urine; water; buffer; groundwater; seawater; rainwater; sap; animal tissue homogenate, extract, or pressing; plant tissue homogenate, extract, or pressing; wastewater; an industrial process fluid or fluid product; fermentation broth; crystallization or precipitation fluid; a food or food process intermediate (e.g., a fermented beverage); oil; inorganic solvent; organic solvent; ionic solvent; honey; syrup; lymphatic fluid; serum; lysate; and the like.

In some embodiments of method 500, the design for the CIF device may be configured effective to passively conduct microfluidic fluid flow as one or more of: gravitational flow, vacuum flow, electroosmotic flow, electrokinetic flow, mechanically pumped flow (e.g., using a syringe pump), and the like. The design for the CIF device may be configured such that a volumetric flow of the central channel flow output and a volumetric flow of the at least one side channel output are substantially equal.

Figure 6:
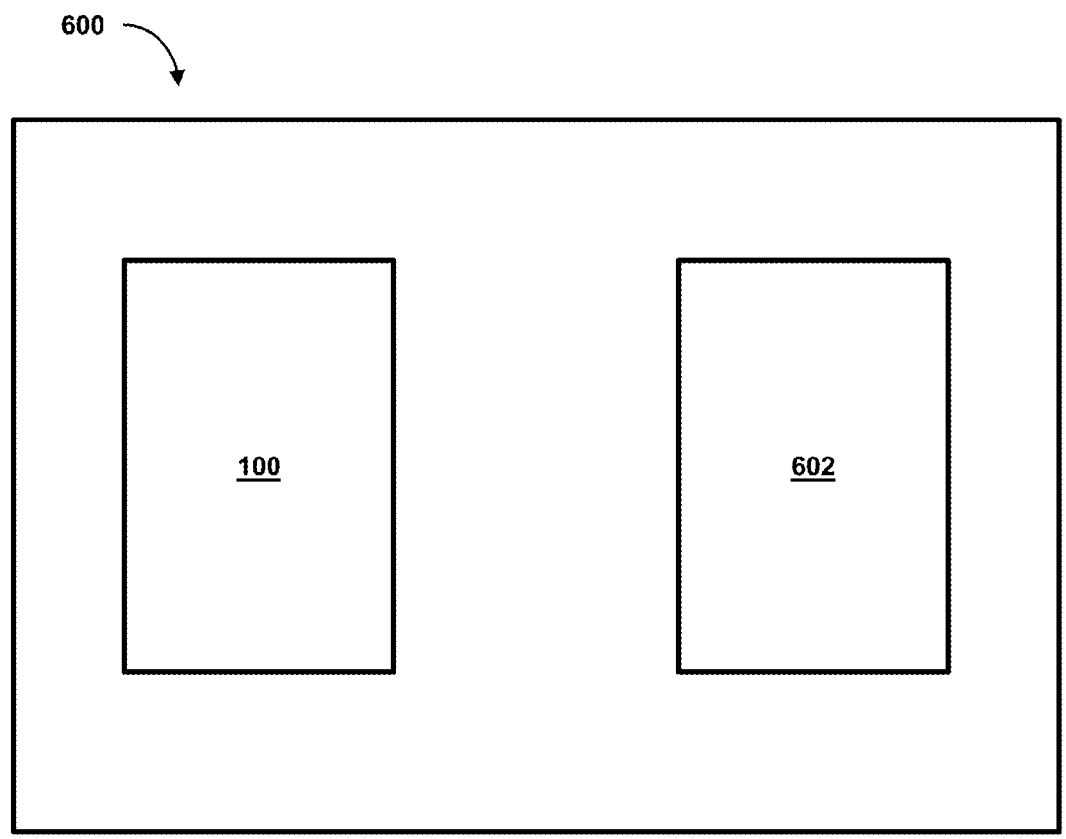
FIG. 6 is a block diagram illustrating an exemplary kit including a CIF device and instructions for conducting an exemplary method for controlled incremental filtration.

FIG. 6 is a block diagram illustrating a kit 600. Kit 600 may include any aspects of the CIF devices described herein, e.g., CIF device 100. For example, kit 600 may include CIF device 100 configured for modulating a concentration of particles 102 of a desired size in a microfluidic flow 104. CIF device 100 may include substrate 106. Substrate 106 may include at least one CIF module 108. Substrate 106 may define in each CIF module 108 a central channel 110. Central channel 110 may extend along a flow path 112 between a central channel flow input 114 and a central channel flow output 116. Substrate 106 may define a plurality of micro-features 122 adjacent to central channel 110. Plurality of micro-features 122 may define a plurality of gaps 124. Plurality of micro-features 122 may separate central channel 110 from at least one side channel network 117. Plurality of gaps 124 may be configured to fluidically couple central channel 110 to at least one side channel network 117. Side channel network 117 may extend along central channel 110 to at least one side channel output 120. Side channel network 117 may include one or more of a first side channel network portion 117a and a second side channel network portion 117a.

In CIF device 100, first side channel network portion 117a may include: a plurality of side channel curves 119 adjacent to central channel 110, at least a portion of plurality of micro-features 122a, and at least a portion of plurality of gaps 124a. Plurality of side channel curves 119 may be characterized by a corresponding plurality of lengths 121a that decrease along flow path 112. Each side channel curve 119 may fluidically couple at least one gap of plurality of gaps 124a in first side channel network portion 117a to one or more of: an adjacent gap in the plurality of gaps 124a and an adjacent curve in the plurality of curves 119.

In CIF device 100, second side channel network portion 117b may include: a side channel 118 adjacent to the central channel 110, at least a portion of plurality of micro-features 122b, and at least a portion of plurality of gaps 124b. Side channel 118 may be characterized by a flow cross-section 139. Flow cross-section 139 may increase along flow path 112 such that plurality of gaps 124b in second side channel network portion 117b are characterized by one or more of: a consistent flow fraction $f_{gap}$ and a plurality of different gap volumetric flow rates.

In CIF device 100, at least one side channel network 117 may be characterized by a decreasing flow resistance along at least a portion of flow path 112 effective to modulate the concentration of particles 102 of the desired size in microfluidic flow 104.

Kit 600 may include may include a set of instructions 602. Instructions 602 may include directions to a user to carry any aspect of operating a CIF device as described herein, for example, any aspect of method 400. For example, set of instructions 602 may include directions to a user to provide the fluid including particles 102 of the desired size. Instructions 602 may include directions to a user to flow the fluid including the particles of the desired size along a flow path through the central channel. Set of instructions 602 may include directions to a user to decrease flow resistance along at least a portion of the flow path effective to modulate the concentration of particles by contacting the fluid comprising the particles of the desired size to the plurality of gaps. Set of instructions 602 may include directions to a user to select the plurality of gaps including an average flow cross-section larger with respect to the particles of the desired size. Set of instructions 602 may include directions to a user to cause different gap volumetric flow rates among at least a portion of the plurality of gaps. Set of instructions 602 may include directions to a user to cause a consistent flow fraction $f_{gap}$ in the central channel to traverse each gap in the plurality of gaps and flow through the at least one side channel network along the flow path In various embodiments, the CIF devices described herein may promote efficiency and predictability of particle concentration in the central channel by permitting an equal amount of fluid to be taken by each side channel network from the central channel, for example, in embodiments including at least two side channels.

In some embodiments, the methods of CIF device design described herein may be used to create a CIF device mold using soft lithography, microCNC machining, laser ablation, or other well-known mold making techniques. Such techniques may simplify the design process and may allow creation of a device by changing a few, e.g., one or two parameters. The methods of CIF device design described herein may promote rapid prototyping. The methods of CIF device design described herein may facilitate production of longer CIF device flow paths capable of greater particle enrichment compared to shorter flow paths. The methods of CIF device design described herein may be simpler than complex CFD modeling techniques that may be computationally limited to a few dozen filtration points or gaps. By comparison, the methods of CIF device design described herein may be less computationally demanding and may be used to quickly generate designs including many thousands of filtration points. The methods of CIF device design described herein may reduce the number of design parameters compared to such complex CFD modeling techniques, facilitating a fast, recursive, numerical approach to generate a CAD drawing for a desired CIF device. The methods of CIF device design described herein may also be more effective than such complex CFD modeling techniques, particularly with respect to predicting effectiveness of contemplated CIF designs. The methods of CIF device design described herein may permit devices of desirable volumetric throughput that may be driven by moderate pressure, passive methods, e.g., by gravitational pressure.

In several embodiments, the CIF devices described herein may concentrate particles above a desired size in a central flow channel compared to adjacent side channels. The central channel and side channels may be separated by gaps, which may be several times larger than the particles of interest, in contrast to known crossflow filtration, which may rely primarily on simple size exclusion. The CIF devices described herein may include side channels having a width that gradually increases along the flow path of the device to provide a filtration size cutoff corresponding to the particles of desired size. This architecture may facilitate calculation of dimensions suitable to provide a consistent filter fraction $f_{gap}$ at each gap. The methods of CIF device design described herein may, by numerically determining the side channel width, permit larger gaps as the filtration points compared to known design techniques. Accordingly, the methods of CIF device design described herein may permit construction of CIF devices with deeper channels compared to known design techniques, which may mitigate or avoid feature collapse or adhesion upon de-molding.

In various embodiments, analytical solutions may be used to generate a CAD drawing in a two-step process of identification followed by implementation. Predictions of flow dynamics often fail, for example in known CFD techniques, so a test step according to the methods described herein may facilitate choosing a suitable $f_{gap}$ value for manufacturing a complete design with the desired total degree of filtration/enrichment. The quick generation of CAD designs with many filtration points enables one to filter to a higher degree in a single device and/or enrich smaller particles.

By controlling the fraction of central channel fluid that flows through each filtration point ($f_{gap}$), the methods and devices described herein permit the use of gaps much larger than the particle(s) of interest, without losing a significant amount of the particles to the side channels of the device. Such large gaps may permit the manufacture of deeper devices, which may increase throughput and expand available applications of the CIF devices. For example, the methods of CIF device design described herein may provide an effective CIF device in a manageable footprint capable of more than just 'lab on a chip' applications, for example, even while the size of the relevant particle of interest may be much smaller, such as with platelets. The methods of CIF device design described herein may provide CIF devices that are more adjustable compared to macroscopic crossflow filtration. The methods of CIF device design described herein may permit the CIF devices to be made out of inexpensive materials such as injection molded plastics without highly-specialized filtration membranes.

EXAMPLES

Experimental Considerations for Device Design and Fabrication

The CIF devices described herein may retain or deplete particles of a specified size from a complex aqueous suspension or slurry. As shown in FIGS. 1-E and 1-F, the central flow channel may have a constant width ($w_c$) and may be flanked by side channels having a width immediately downstream of gap i, $w_s(i)$ corresponding to a desired value of $f_{gap}$, and the side channel width immediately downstream of the preceding gap, $w_s(i-1)$. This recursive approach to calculating the side channel width may permit a CAD drawing of a device design to be built up quickly, using a small number of governing equations and simplifying assumptions. For example, an assumption permitting an easily-implementable model is to treat the space between gaps as nodes that may allow equalization of pressure across the width of the device. Without wishing to be bound by theory, it is believed that relatively large-mouthed (~20 μm) gaps may be used, which present only a small amount of resistance to the small amount of flow of fluid through each gap, facilitating pressure equilibration, for example, with main channel widths on the order of 100 μm. Without wishing to be bound by theory, it is believed that devices that remove on the order of 0.05% of the fluid from the central channel at each gap (i.e., $f_{gap} \sim 5 \times 10^{-4}$) may be desirable. Accordingly, a recursive equation for volumetric flow in the side and central channels at gap i, [$Q_s(i)$ and $Q_c(i)$, respectively] may be used. Once expanded, the recursive equation may describe the growth in side channel width along the length of the device corresponding to a consistent, e.g., constant, $f_{gap}$:

$$Q_s(i) = Q_s(i-1) + f_{gap} \cdot Q_c(i-1)$$

The preceding relation may be expressed in terms of pressure differential between gap i and gap i+1, $\Delta P(i)$, the resistance of a side channel segment immediately downstream of gap i, $R_s(i)$, and the central channel segment resistance, $R_c$, as:

$$\frac{\Delta P(i)}{R_s(i)} = \frac{\Delta P(i-1)}{R_s(i-1)} + f_{gap} \cdot \frac{\Delta P(i-1)}{R_c}$$

Assuming an incompressible fluid, the sum of volumetric flows through the three channel segments of a CIF device with two side channels may equal a constant. Accordingly, a ratio of $\Delta P(i-1)$ to $\Delta P(i)$ may equal $(1 - 2 \cdot f_{gap})^{-1}$. The preceding relation may be reformulated as:

$$R_s(i) = \frac{1 - 2 f_{gap}}{\frac{1}{R_s(i-1)} + \frac{f_{gap}}{R_c}} \quad \text{(eq. 1)}$$

For example, the method for determining the width of the side channels may begin with an arbitrary side channel width at i=1, e.g., close or equal to zero. Subsequently, eq. 1 may be used to determine the width of subsequent side channels, $w_s(i)$ by adding a small amount to the value of $w_s(i-1)$ until the value of $R_s(i)$ according to eq. 2 below also satisfies eq. 1. This approach may be encoded in any number of software packages capable of numerical solutions, such as MATLAB (MathWorks, Natick, Mass.).

The fluidic resistance (R) of each channel segment may be calculated from a corresponding width (w) and depth (d) via an analytically-derived solution for a rectangular channel:

$$R(w, d, \mu, L) = \frac{12 \mu L}{dw^3} \left[ 1 - \frac{192 w}{d} \cdot \sum_{n=1,3,5,\ldots}^{\infty} \frac{\tanh\left(\frac{n \pi d}{2w}\right)}{(n\pi)^5} \right]^{-1} \quad \text{(eq. 2)}$$

where μ is the viscosity of the fluid, and L is the channel length, which in one embodiment is simply assumed to equal the length, along the direction of flow, of a micro-feature, e.g., a micro-pillar in the device, as shown in FIG. 1-F. In various examples, neither of μ or L affects the side channel width calculation, where the values of μ and L may be considered to be constant across the channel segments. Without wishing to be bound by theory, the assumption that the value of μ may be considered to be constant across the channel segments may not correspond to particulate solutions that are highly concentrated in the central channel and depleted in the side channels. In various examples, d and w can be reversed in the equation without affecting the validity of eq. (2), thus making the solution aspect ratio independent, in contrast to other treatments of R(w).

FIGS. 10-A-D are a series of plots illustrating the relationship between the progressive increase in side channel width along the length of a device, calculated as a function of device depth and $f_{gap}$. Each curve in FIGS. 10-A-D was generated using only equations 1 and 2 above, with an initial side channel width of zero and a central channel width of 100 μm.

Example 1

CIF Device Fabrication

Desired device parameters were input into custom-written MATLAB software and the resultant design feature coordinates were exported for generating a CAD of each device. Chrome-on-glass photomasks of the CAD device designs were then used to pattern the microchannel patterns into photoresist (SU8 3050, ~100-150 μm deep) spun onto standard 4" silicon wafers and subjected to UV (i-line) exposure. Inverse polydimethylsiloxane (PDMS; SylGard 184, Dow Corning, Midland, Mich.) molds of the wafer/photoresist masters were created and sealed to PDMS-coated glass slides via air plasma oxidation. Input and output fluidic ports were created in the ~5 mm thick PDMS via biopsy punches prior to sealing. PDMS devices were then treated with polyethylene glycol (PEG) prior to the introduction of the particulate suspensions of interest. Fluid was driven through the devices by inserting into the input port an appropriate length of 1.5 mm-diameter polyethylene tubing, which was attached to a 10 mL plastic vessel and hung at heights between 1 inch to 5 feet above the device. Both the tubing and vessel were filled with a liquid buffer appropriate for the particle type(s) being studied. After a sufficient volume of fluid had passed through a given device, samples were collected from each of the output ports for analysis.

Though the above method incorporates one standard method for rapid prototyping bench-scale microfluidic devices, larger and more durable metal master molds may also be created e,g, via electroforming. Such metal master molds may be more appropriate for mass producing plastic devices via e.g. injection molding or hot embossing, since producing devices by curing PDMS is time consuming and not cost-effective in many applications. Other methods known to the art for mass producing polymeric devices may also be used.

Example 2A

CIF Two-Step Design Process for Polystyrene Bead Separation

In a first step, a number of filtration channels were tested in parallel, each with a different value of $f_{gap}$. By observing which particles were maintained or not maintained in the central channel as a function of $f_{gap}$, the appropriate $f_{gap}$ value was selected for use in patterning a complete device in step two.

Figure 11:
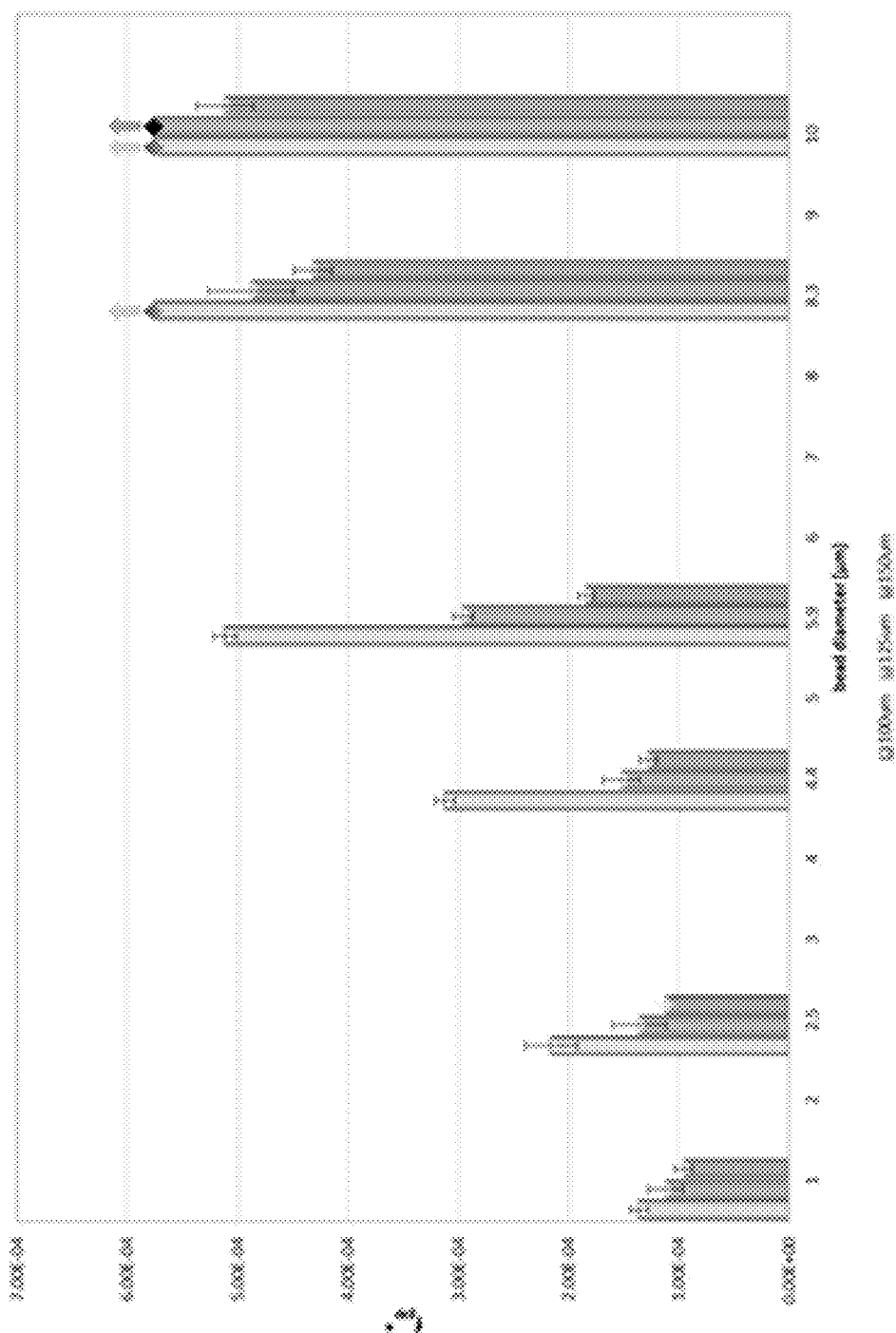
FIG. 11 is a bar graph demonstrating shows the effect of central channel width on flow fraction $f_{gap}$.

FIG. 11 presents the results of performing step one on beads of various diameters in three microchannel arrays with different central channel widths (100 μm, 125 μm, and 150 μm). In each case, a parallel array of 33 test devices was designed to explore a wide range of the degree filtration per gap, with device $f_{gap}$ values ranging linearly from $6.4 \times 10^{-5}$ (device #1) to $5.76 \times 10^{-4}$ (device #33). Arrays of devices with the given parameters were designed according to eqs. 1 and 2 and created for testing. Values for the $f_{gap}$ cutoff threshold ($f_{gap}*$) for polystyrene beads of various diameters were determined visually by observing the $f_{gap}$ below which the beads were consistently maintained in the central flow channel. As the width of the central channel increased or the size of the particle decreased, the $f_{gap}$ limit at which particles begin to be dragged along with fluid flow through the gaps was observed to decrease. A range of $f_{gap}$ values was also tested in order to determine a desired value for the particle of interest.

Example 2B

Figure 12B:
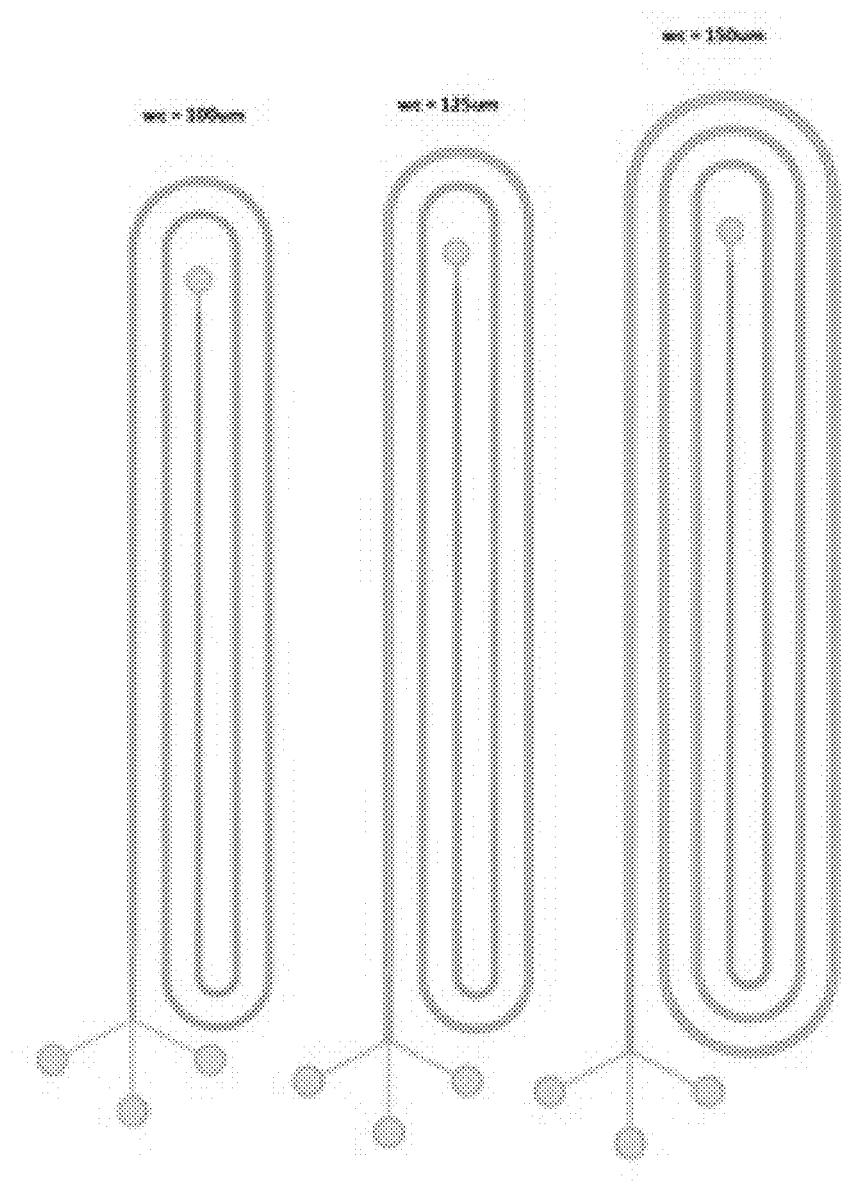
FIGS. 12-A, 12-B, and 12-C demonstrate a two-step process for the efficient creation of a platelet enrichment device.
Figure 12C:
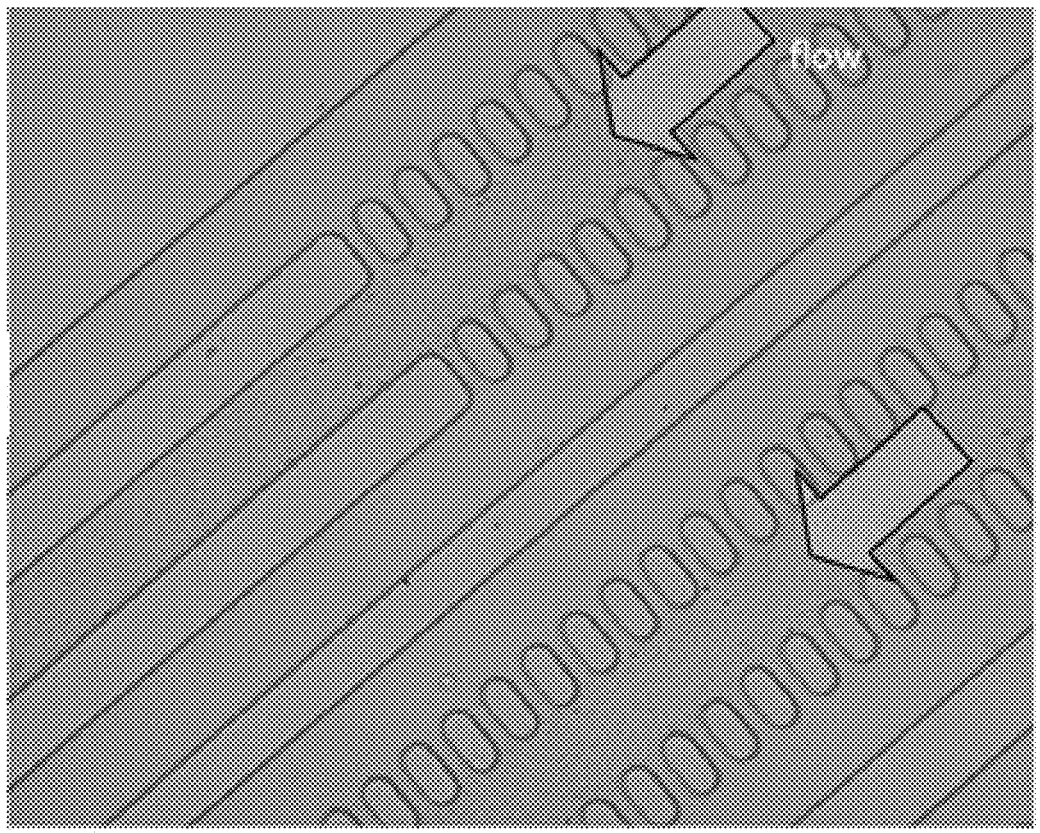

Application of CIF Two-Step Design Based on Polystyrene Bead and Platelet Separation The results in Example 2A give approximate guiding values useful for investigating particle enrichment/filtration applications more complex than simple beads in saline solution. One such application of keen practical interest is further enrichment of platelets in a suspension of PRP to levels above the AABB standard for PC. Platelets have an approximately discoid but also highly variable, non-uniform and dynamic shape, with effective diameters of ~1.5-4 μm. The behavior of PRP flowing through the same three arrays as described in FIG. 11 was investigated, with particular attention to devices in the range of #2 to #10, corresponding to $f_{gap}$ values ~$1$-$2 \times 10^{-4}$. The platelets of the subjects studied consistently remained in the central flow channel for devices below #9 (for $w_c$=100 μm), #8 (125 μm), and #5 (150 μm), corresponding to $f_{gap}*$ values of $1.92 \times 10^{-4}$, $1.76 \times 10^{-4}$ and $1.28 \times 10^{-4}$, respectively. FIG. 12-A demonstrates a difference between platelets flowing through devices #4 and #5, showing at the transition between a lossless degree of filtration and an excessive degree of filtration took place around device #5 (with $w_c$=150 μm and d=150 μm). The platelets were not observed to be present in the inter-obstacle gaps in the left-side panel (device #4) but are observed in the right-side panel (device #5), which indicates $f_{gap}$ had become larger than desirable in device #5.

Example 3A

Enriching Platelets in a PRP Suspension after Sedimentation of RBCs

Figure 7A:
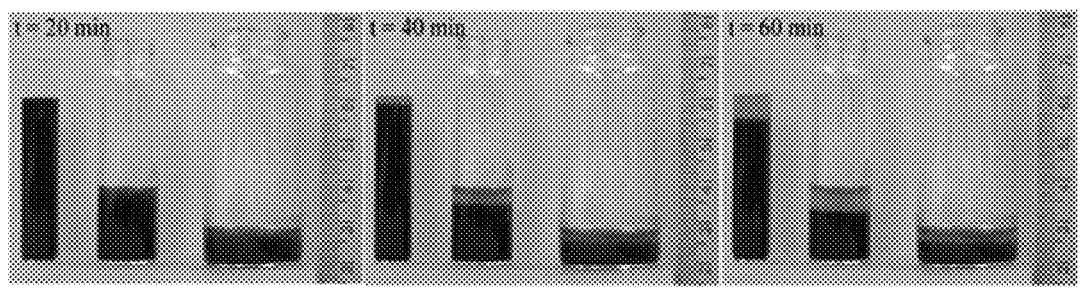
FIG. 7A depicts sedimentation of WB according to aspect ratio of various vessels for equivalent volumes of WB (3 mL).
Figure 7B:
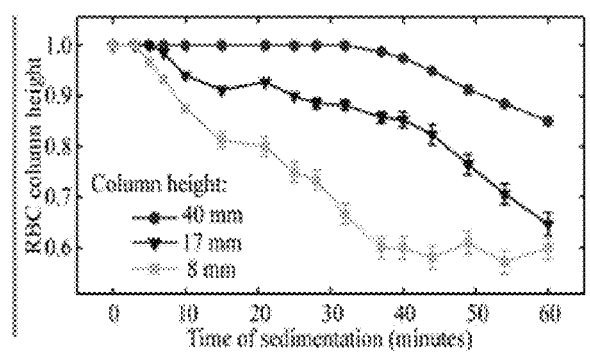
FIG. 7B is a graph showing the dependence of sedimentation speed on aspect ratio of the vessel for equivalent volumes of WB (3 mL).
Figure 9:
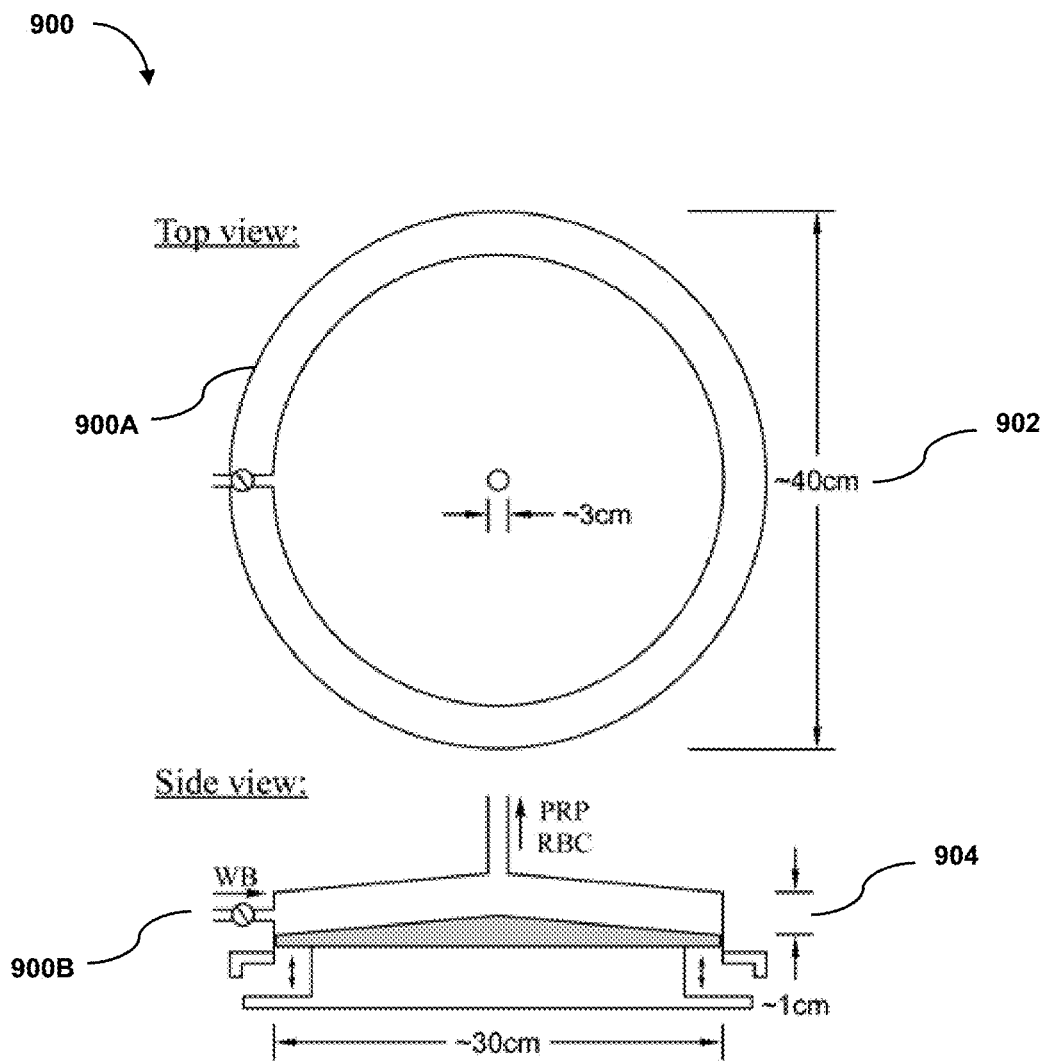
FIG. 9 shows an exemplary Stage 1 module for separating a 500 mL unit of WB into RBCs and PRP using 1×g sedimentation.

The guiding values for $w_c$ and $f_{gap}$ established for bead and platelet enrichment in Examples 2A, 2B were used to design a longer CIF device, via eqs. 1 and 2 above, with the goal of filtering a desired amount of plasma out of a sample of PRP while retaining PC in the central channel for collection. The CIF device thus designed was used in conjunction with the following sedimentation process for separating WB into RBCs and platelet-rich plasma (PRP). Sedimentation dynamics were compared for 3 mL volumes of fresh, human WB [Hematocrit (HCT)=0.42; Platelet count (PLT)=409×10³/µL] in cylindrical vessels with different inner diameters (corresponding WB column heights: 40, 17 and 8 mm). RBCs in the short/wide 8 mm column achieved sedimentation in about 35 minutes, and the 17 mm-high column had nearly finished sedimentation in 60 minutes, while the tall/narrow 40 mm column continued to settle, as depicted in FIG. 7A and as graphed in FIG. 7B. In all three vessels, packed RBCs had HCT of ~0.7 and PLT ranging from 83-123×10³/µL (lower than WB). The layer of PRP had PLT within 1,093-1,174×10³/µL, which implies that platelets were being actively extruded from the layer of packed RBCs during sedimentation. FIG. 9 is a schematic showing a wide aspect ratio vessel 900, including a width 902 and a depth 904. This example demonstrates that 500 mL of WB can be completely separated at 1×g into packed RBCs and PRP in less than 60 minutes, if WB is spread into an about 10 mm-high cylindrical column in a vessel with a diameter of about 25 cm, as shown in FIG. 9.

Figure 8:
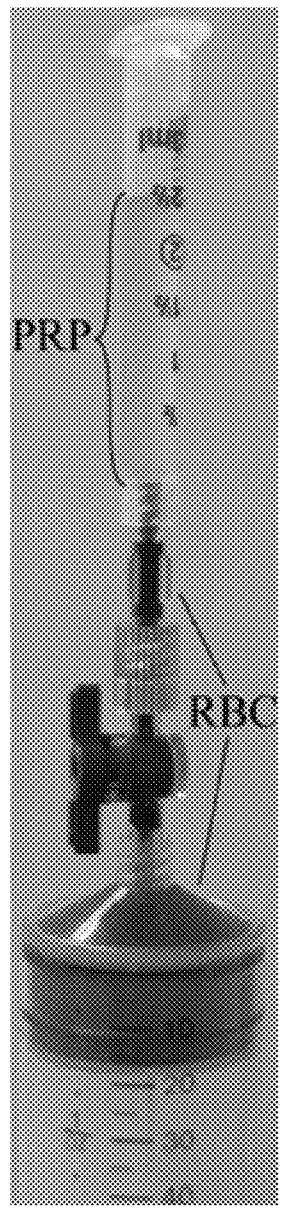
FIG. 8 depicts an exemplary PRP layer expressed into a 3 mL syringe after 55 minutes of sedimentation.

Additional experiments were performed using a modified 140 mL syringe on 8 mL volumes (~10 mm column height) of WB from 7 different donors (4 female, 3 male). The parameters of WB among the subjects varied significantly (HCT=0.42±0.02, PLT=220±96×10³/µL, platelet activation 3.8%). For each experiment, after 55 min of sedimentation, the PRP layer was expressed into a 3 mL syringe, as shown in FIG. 8. The average HCT of the resultant packed RBC fractions was 0.67±0.06 and the supernatant PRP had platelet activation of ~5% and a mean PLT value of 552±174K/µL, corresponding to a 2.5-fold enrichment. No hemolysis was observed.

Example 3B

Design of a Device for Sedimentation of RBCs

The dependence of sedimentation time $T_s$ and HCTRBC (HCT of the RBC fraction) on the height of the WB column were measured. The heights of test WB columns were varied between 5 mm to 15 mm in cylindrical vessels using 10 mL volumes of fresh WB collected from consenting volunteers (n=10, male and female to capture the inter-gender differences of RBC sedimentation). The dependence of $T_s$ and HCTRBC on the shape of the sedimentation vessel for a given WB column height of either 5 mm, 10 mm, or 15 mm using vessels shaped as a traditional cone or inverted cone with the opening angle of the cone ranging from 30° to 180° were quantified. Cone-shaped vessels were fabricated by casting appropriately shaped molds produced using a 3D prototype printer in silicone elastomer (Rhodorsil V-1082, condensation-cure PDMS with a tin-based catalyst, Bluestar Silicones, York, S.C.). In one example, the Stage 1 device module was fabricated via standard injection molding techniques and sterilized using gamma radiation. The Stage 1 module was capable of accepting donated WB directly or from a standard blood collection bag. The Stage 1 module initiated the RBC separation immediately upon filling.

Example 3C

Products of RBC Sedimentation

After $T_s$ ~60 minutes at rest in normal gravity, whole blood passively separated into components with packed RBCs on the bottom and a PRP overlayer. The PRP was expressed out of the top of the slightly tapered device after RBC sedimentation was complete to minimize mixing of the biphasic solution after sedimentation. The PRP was directed to a CIF-based device for further processing as described in Example 3D. The heavier, more viscous RBC layer was expressed into a standard blood bag for hypothermic storage.

Example 3D

PRP Enrichment Using the CIF Device

In the second step of CIF device design for the platelet enrichment application, the three threshold values of $f_{gap}$ found in step one from Example 2A, 2B above were used to pattern complete devices for each of the corresponding central channel widths. Associated final side-channel widths were selected to produce the desired level of particle enrichment after a single pass through a given device. Approximately 70% of the total volume of the input PRP was targeted for removal and the final side-channel widths were calculated using eq. 2 above such that the ratio of side-channel flow resistance to center channel flow resistance produced the desired relative volumetric flow rates in each channel at the end of the device. Removing approximately 70% of the total volume of fluid from the input sample was expected to increase the particle count in the main channel by about 3.33 times, if no particles were lost with the removed fluid. FIG. 12-B shows the three complete devices to scale, generated by software written according to the modeling approach described above, with the flow path of each device incorporating several turns to fit onto a standard 4" wafer via photolithography. Each turn may include appropriate modification of the side channel widths through the course of the turn effective to avoid by an inner channel of the turn having a shorter overall path length (and thus resistance) than a channel further from the focal point of the turn.

The smaller the value of $f_{gap}*$, the longer the device must be to achieve a desired total amount of filtration. For this example, a 125 µm wide central channel with a $f_{gap}*$ value of $1.76 \times 10^{-4}$ was selected as optimal after considering also the increased throughput which generally accompanies a higher value of $w_c$. An application having desired particles of much smaller effective size would be expected to use a more conservative filtration fraction per gap. FIG. 12-C shows a representative image of the output of the device created based on these parameters. The input platelet count (PLT) was 354K/µL, the combined output PLT value of the side channels was 68K/µL, and the central channel output was 999K/µL. These results demonstrate that the PLT of the sample was increased ~3-fold, with very little loss (<15%) of platelets to the side channels.

Example 4

Retaining Beads of a Defined Size in the Central Channel

A device was created with a 125 µm wide central channel with an $f_{gap}$ value of $4.52 \times 10^{-4}$ and channel depths of 150 µm to demonstrate concentration of particles above a certain size within an overall complex mixture. The device was patterned with the width of the side channels increasing to 2.5× the central channel along the flow path, corresponding to a flow rate ~5× higher than the central channel. Beads with a diameter of 8.3 µm were added to a PRP suspension and run through the device, resulting in ~90% removal of the original volume of fluid.

Figure 13A:
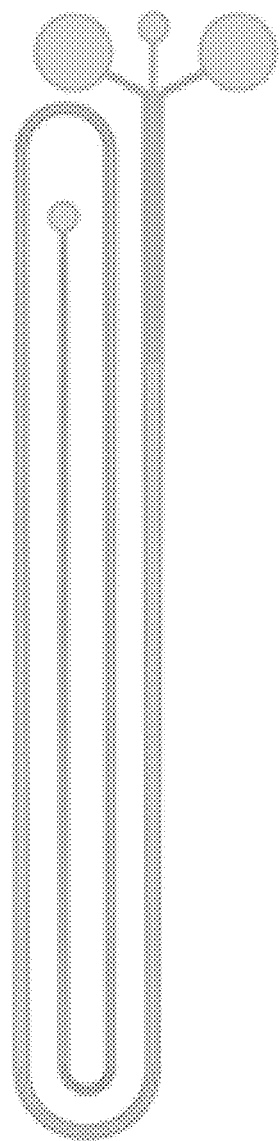
FIGS. 13-A, 13-B, and 13-C illustrate a CIF device. A value for $f_{gap}$ was selected corresponding to retaining particle diameters between 5.9 μm to 8.3 μm and was used to pattern a full-length device with a total filtration fraction of ~90%.
Figure 13B:
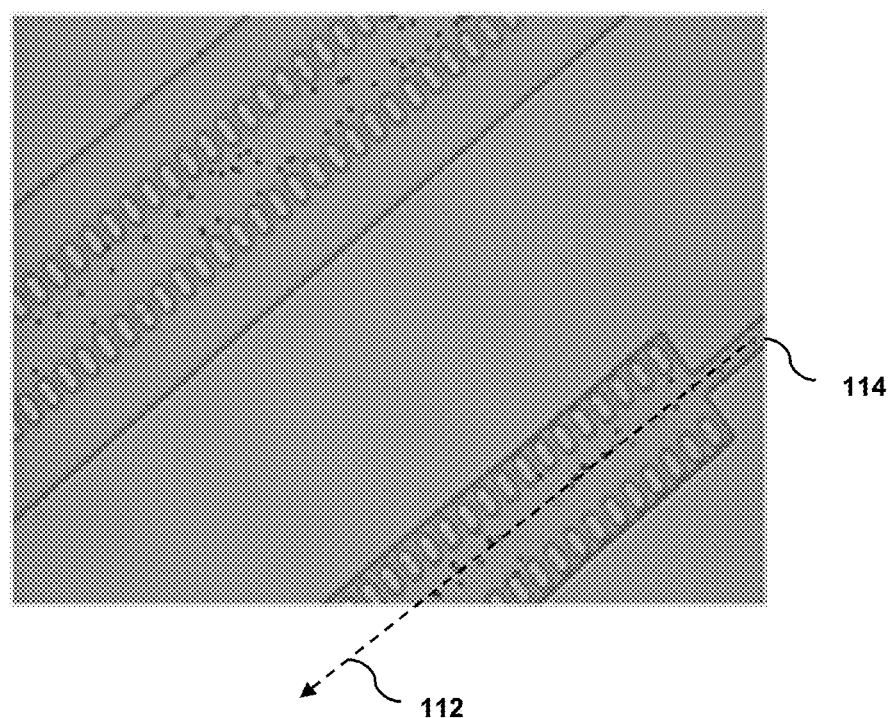
Figure 13C:
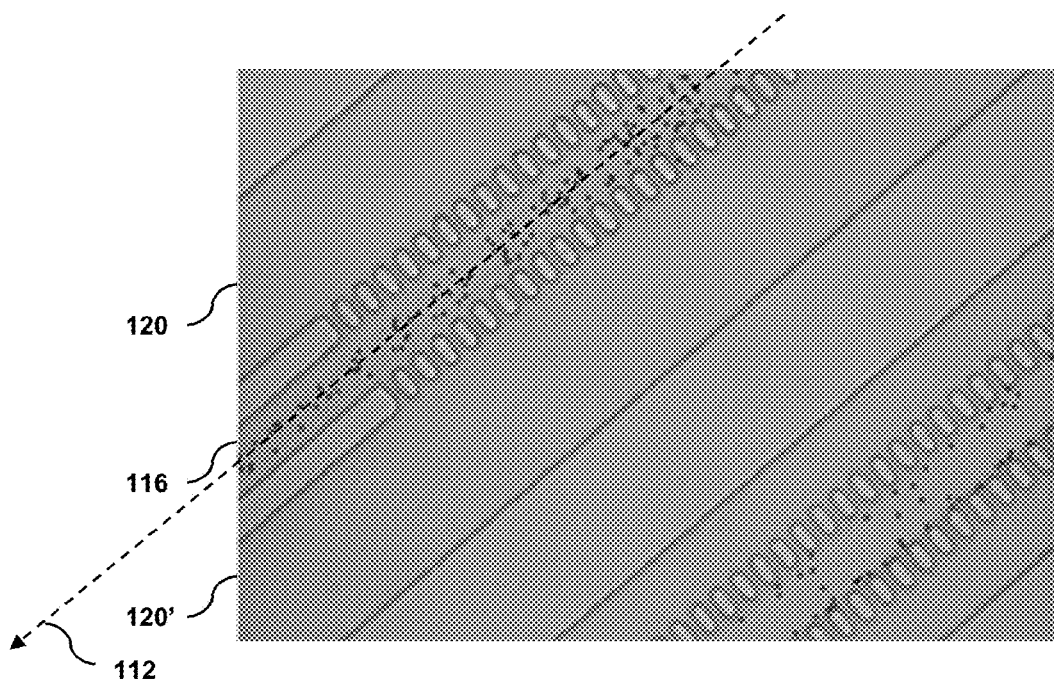

FIG. 13 shows the schematic of the device and a representative image of the flow into output collection channels. This example shows that the platelets, which are typically under 4 μm in diameter, were pulled into the side/filtration channels, while the larger 8.3 μm beads were maintained in the central/concentration channel, consistent with the step one test results shown in FIG. 11. Thus, larger particles were more heavily concentrated using the CIF approach in the same device footprint according to the corresponding larger value of $f_{gap}*$ relative to the smaller platelets. This example demonstrates that size-specific subpopulations can be enriched out of a mixture of variously-sized particles using a CIF-based device. Several such devices may be employed in series to effect a more complex selective removal or enrichment of a desired range of particle sizes, for example, to separate or concentrate particles in a range, e.g., above 3 μm and below 10 μm.

Example 5

Input Design of a CIF Device to Facilitate Large-scale Manufacture

The side-channel width at the beginning of a CIF device may be designed to begin very close to, or at, zero. The device shown in FIG. 13-B has an initial side channel width of ~8 μm. However, such an initial width may undesirably divert particles desired for concentration into the side channels. In practice, micro-device construction via photolithography or other methods may be limited by the smallest feature size within the design. It may be useful to make the minimum feature size as large as possible to facilitate device manufacture. In general, larger minimum feature sizes increase the depth of the channels which can be feasibly fabricated. This may correspond to an upper practical limit to an aspect ratio of a microdevice, according to the technical constraints of both master mold fabrication and the ability to reliably extract parts molded of substrates such as PDMS, thermoplastic, etc. from the mold.

In one example of increasing the minimum feature size of a CIF device, the design considerations may be adapted at the input of the device by adjusting the length of the side-channel, rather than its width (which is the case described in preceding Examples). result of This is shown in FIG. 1-B for one particular CAD design. Here, eq. 1 was used to determine the side channel dimensions at each filtration point. The side channel width was initially set to be equal to the gap size of the designed array. Progressive decreases in side channel resistance were achieved by decreasing the total side channel length at each filtration point at every other gap in the device architecture. Analogous to the width-dependent calculation described in preceding Examples, a small amount may be iteratively subtracted from an initial value of the side channel length. The initial length was set at a large value relative to the central channel dimensions to provide a minimal amount of fluid flow into the side channels at the first opening. The small amount was iteratively subtracted from the initial value of the side channel length until the value of the side channel resistance calculated in eq. 2 satisfies eq. 1. This process was repeated at each filtration point. The custom-written software constructed the side channel of the calculated length by drawing a side channel that directs its fluid flow first away from, and then back toward, the main flow of the device, as shown in Figure XYZ. More advanced formulation of eq. 2 may facilitate an accurate estimate of side channel resistance, considering the non-linearity of the side channel geometry. This approach may be encoded in the CIF device design software to take place at the start of a device until the calculated side channel segment length is no larger than the corresponding central channel segment length. After that point in the CIF design process, the side channel widths would be allowed to progressively increase, as described in the above Examples.

Prophetic Example 6

Design of a CIF Device with Decreasing Central Channel Width

In some applications or embodiments, it may be desirable to also progressively decrease the central channel width while increasing the side channel width. This may be done either while maintaining the total device width or not. This type of modified approach and similar formulations can be encoded into software for subsequent CAD drawing and device manufacture by employing the same incremental calculations described for the constant width central channel examples described above.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "operatively coupled" or "operatively connected" are used in the specification or the claims, it is intended to mean that the identified components are connected in a way to perform a designated function. Further, for example, to the extent that the terms "fluidically coupled" or "fluidically connected" are used in the specification or the claims, it is intended to mean that the identified components are connected in a way to permit exchange or transfer of a fluid or a fluid property, e.g., to provide fluid flow, to transmit fluid pressure, and the like. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A controlled incremental filtration (CIF) device configured for modulating a concentration of particles of desired size in a fluid in microfluidic flow, comprising:
  a substrate comprising at least one CIF module, the substrate defining in each CIF module:
    a central channel, the central channel extending along a flow path between a central channel flow input and a central channel flow output;
    a plurality of micro-features adjacent to the central channel, the plurality of micro-features defining a plurality of gaps, the plurality of micro-features separating the central channel from at least one side channel network, the plurality of gaps configured to fluidically couple the central channel to the at least one side channel network, the at least one side channel network extending along the central channel to at least one side channel output, the at least one side channel network comprising one or more of:
      a first side channel network portion comprising: a plurality of side channel curves adjacent to the central channel, at least a portion of the plurality of micro-features, and at least a portion of the plurality of gaps;
        the plurality of side channel curves being characterized by a plurality of lengths that decrease along the flow path, each side channel curve fluidically coupling at least one gap of the plurality of gaps in the first side channel network portion to one or more of: an adjacent gap in the plurality of gaps and an adjacent curve in the plurality of curves; and
      a second side channel network portion comprising: a side channel adjacent to the central channel, at least a portion of the plurality of micro-features, and at least a portion of the plurality of gaps;
        the side channel being characterized by a flow cross-section that increases along the flow path such that the plurality of gaps in the second side channel network portion are characterized by one or more of: a consistent flow fraction $f_{gap}$ and a plurality of different gap volumetric flow rates;
        the at least one side channel network being characterized by a decreasing flow resistance along at least a portion of the flow path effective to modulate a concentration of particles of a desired size in a fluid in microfluidic flow through said device.

2. The CIF device of claim 1, comprising two of the side channel networks, the two side channel networks being adjacent to the central channel and the two side channel networks being separated by the central channel.

3. The CIF device of claim 1, the plurality of gaps in each of the CIF module being characterized by an average gap cross-sectional area parallel to the flow path, the average gap cross-sectional area being sized compared to the particles of desired size effective to one or more of:
  mitigate or eliminate fouling of the plurality of gaps by the particles; and
  mitigate or eliminate steric exclusion of the particles by the plurality of gaps.

4. The CIF device of claim 1, comprising one or more of the following:
  the central channel in each of the CIF modules being fluidically coupled to an input source through the central channel flow input;
  the at least one side channel network being fluidically coupled to the input source through the plurality of gaps to the central channel;
  the central channel in each of the CIF modules being fluidically coupled to a retentate output reservoir; and
  the at least one side channel network in each of the CIF modules being fluidically coupled to a filtrate output reservoir.

5. The CIF device of claim 1, the flow path in each of the CIF modules comprising one or more turns in the substrate.

6. The CIF device of claim 1, the second side channel network portion being characterized by a ratio of a cross-sectional area of the at least one side channel to a cross-sectional area of the central channel, the cross-sectional areas, being perpendicular to the flow path, the ratio increasing along at least a portion of the flow path.

7. The CIF device of claim 1, wherein each of the CIF modules is characterized along the second side channel network portion by a flow cross-sectional area of the central channel perpendicular to the flow path, the flow cross-sectional area of the central channel being constant, increasing, or decreasing along the flow path, or
  each of the CIF modules is characterized along the second side channel network portion by a flow cross-sectional area of the at least one side channel perpendicular to the flow path, the flow cross-sectional area of the at least one side channel being constant, increasing, or decreasing along the flow path.

8. The CIF device of claim 1, each of the CIF modules being configured, upon conducting the microfluidic flow using a mixture of 1% w/w 4 µm polystyrene microbeads in water at a temperature of 25° C. and a flow pressure of 2 PSI, to concentrate the particles of the desired size in the microfluidic flow from a starting particle concentration at the central channel flow input to a final concentration at the central channel flow output by a concentration factor of at least 1.5:1.

9. The CIF device of claim 1, each of the CIF modules being configured to be capable of conducting the microfluidic flow as one or more of: a gravitationally-directed flow, a vacuum directed flow, an electroosmotic directed flow, an electrokinetic directed flow, and a mechanically pumped flow.

10. The CIF device of claim 1, the substrate comprising two or more of the CIF modules, the two or more of the CIF modules being fluidically coupled in series or fluidically coupled in parallel.

11. The CIF device of claim 1, the substrate comprising two or more of the CIF modules, the two or more of the CIF modules being fluidically independent.

12. The CIF device of claim 1, further comprising at least one additional separation device, the at least one separation device fluidically coupled to one or more of: the central channel flow input, the central channel flow output, and the at least one side channel output.

13. The CIF device of claim 12, the at least one additional separation device comprising one or more of: a filter, a centrifuge, an electrophoresis device, a chromatography column, a fluid evaporator, a sedimentation device, a deterministic lateral displacement device, a plasma skimmer, a margination device, a magnetic separator, an ultrasound focusing device, and a density gradient separator.

14. A method for making the CIF device of claim 1, comprising:
   i) preparing an initial design for the CIF device;
   ii) selecting a desired flow fraction $f_{gap}$ for the CIF device;
   iii) determining a plurality of adjusted dimensions along the flow path;
   iv) adapting said initial design to incorporate the plurality of the adjusted dimensions effective to provide a decreasing flow resistance along at least a portion of the flow path effective to modulate the concentration of particles of the desired size in the fluid, thereby providing a complete design for the CIF device; and
   v) fabricating the CIF device according to said complete design.

15. The method of claim 14, the adjusted dimensions along the flow path comprising one or more of:
   in a first side network portion, a decreasing length of each of a plurality of side channel curves, the plurality of side channel curves being adjacent to the central channel in the first side channel network portion; and
   in a second side network portion, an increasing ratio of a cross-sectional area of at least one side channel to a cross-sectional area of the central channel, the at least one side channel being adjacent to the central channel in the second side network portion.

16. The method of claim 14, comprising determining the plurality of adjusted dimensions by:
   (a) determining a central channel flow resistance $R_c$;
   (b) determining a first side channel segment flow resistance corresponding to a first side channel segment between a first pair of adjacent gaps in the plurality of gaps along the flow path, the first flow resistance determined according to a first functional relationship between: a viscosity of the fluid; a first effective side channel width w and a first effective channel depth d corresponding to a first cross-sectional area at the first side channel segment; and a length L of the first side channel segment;
   (c) determining a second side channel segment flow resistance corresponding to a second side channel segment between a second pair of adjacent gaps in the plurality of gaps along the flow path, the second side channel segment being located immediately downstream of the first side channel segment, the second side channel segment flow resistance being determined according to a second functional relationship between: the central channel flow resistance, the first side channel segment flow resistance, and the desired flow fraction $f_{gap}$ for the CIF device;
   (d) recalculating the first functional relationship using one or more adjusted dimensions comprising one or more of: a second effective side channel width w; a second effective channel depth d; and a second side channel length L; the one or more adjusted dimensions being effective to cause the second side channel segment flow resistance according to the second functional relationship to be lower than the first side channel segment flow resistance by a desired amount; and
   (e) conducting steps (b), (c), and (d) for a plurality of iterations to calculate the plurality of the adjusted dimensions.

17. The method of claim 16, wherein recalculating the first functional relationship is comprised of numerically solving the first functional relationship for the one or more adjusted dimensions.

18. The method of claim 16, the first and second functional relationship being represented respectively by:

$$R_s(i) = \frac{1 - 2f_{gap}}{\frac{1}{R_s(i-1)} + \frac{f_{gap}}{R_c}}, \text{ and} \quad \text{(eq. 1)}$$

$$R(w, d, \mu, L) = \frac{12\,\mu L}{dw^3}\left[1 - \frac{192w}{d} \cdot \sum_{n=1,3,5,\ldots}^{\infty} \frac{\tanh\left(\frac{n\pi d}{2w}\right)}{(n\pi)^5}\right]^{-1} \quad \text{(eq. 2)}$$

wherein:
   $R_c$ represents flow resistance of the central channel;
   $R_s(i-1)$ represents flow resistance in a portion of the at least one side network between a gap i−1 and a gap i in the plurality of gaps, i being increased by 1 for each gap in the plurality of gaps along the flow path;
   $R_s(i)$ represents flow resistance in a portion of the at least one side network between the gap i and a gap i+1 in the plurality of gaps;
   $R(w, d, \mu, L)$ represents resistance of a channel segment in a portion of the central channel or the at least one side network;
   w represents a width corresponding to approximating the channel segment as a rectangular channel;
   d represents a depth corresponding to approximating the channel segment as a rectangular channel;
   L represents a length corresponding to approximating the channel segment as a rectangular channel; and
   $\mu$ represents a viscosity of the fluid.

19. A method for CIF of particles in a fluid, comprising:
   introducing a fluid comprising a plurality of particles of a plurality of sizes including at least one desired size to the CIF device of claim 1 at said central channel flow input;
   flowing said fluid comprising said particles from said central channel flow input along said flow path to said central channel flow output; and
   collecting one or more fractions of fluid containing an increased concentration of particles of desired size from said central channel flow output.

20. A method for CIF of particles in a fluid, comprising:
   introducing a fluid comprising a plurality of particles of a plurality of sizes including at least one desired size to the CIF device of claim 4 at said central channel flow input;
   flowing said fluid comprising said particles from said central channel flow input along said flow path to said central channel flow output; and
   collecting one or more of i) retentate fraction from the central channel, ii) a filtrate fraction from the at least one side network, or iii) a fraction of fluid comprising an increased or a decreased concentration of the particles of the desired size.

21. A CIF device is claim 1, wherein the central channel is a concentration channel.

22. A CIF device of claim 1, wherein the central channel is a concentration channel, adjacent to a single filtration channel on one side of the concentration channel.

* * * * *

UNITED STATES PATENT AND TRADEMARK OFFICE
CERTIFICATE OF CORRECTION

PATENT NO. : 9,789,235 B2
APPLICATION NO. : 14/601205
DATED : October 17, 2017
INVENTOR(S) : Sean C. Gifford and Sergey S. Shevkoplyas It is certified that error appears in the above-identified patent and that said Letters Patent is hereby corrected as shown below:

In the Claims

Claim 3 should read:
3. The CIF device of claim 1, the plurality of gaps in each of the CIF modules being characterized by an average gap cross-sectional area parallel to the flow path, the average gap cross-sectional area being sized compared to the particles of desired size effective to one or more of:
    mitigate or eliminate fouling of the plurality of gaps by the particles; and
    mitigate or eliminate steric exclusion of the particles by the plurality of gaps.

Claim 21 should read:
21. A CIF device of claim 1, wherein the central channel is a concentration channel.

Signed and Sealed this
Twelfth Day of December, 2017

Joseph Matal
*Performing the Functions and Duties of the
Under Secretary of Commerce for Intellectual Property and
Director of the United States Patent and Trademark Office*